(12) United States Patent
Christensen et al.

(10) Patent No.: US 6,784,169 B2
(45) Date of Patent: Aug. 31, 2004

(54) MMP INHIBITORS

(75) Inventors: Mette Knak Christensen, Holte (DK); Lars Kristian Albert Blæhr, København (DK)

(73) Assignee: Leo Pharmacetical Products Ltd., Ballerup (DK)

( * ) Notice: Subject to any disclaimer, the term of this patent is extended or adjusted under 35 U.S.C. 154(b) by 6 days.

(21) Appl. No.: 10/345,304

(22) Filed: Jan. 16, 2003

(65) Prior Publication Data
US 2003/0191092 A1 Oct. 9, 2003

Related U.S. Application Data
(60) Provisional application No. 60/349,229, filed on Jan. 18, 2002.

(51) Int. Cl.[7] .............................. A61K 31/66; C07F 9/02
(52) U.S. Cl. .......................................... 514/110; 558/81
(58) Field of Search .............................. 558/81; 514/110

(56) References Cited

U.S. PATENT DOCUMENTS

| | | | |
|---|---|---|---|
| 3,732,340 A | | 5/1973 | Arnold et al. |
| 4,605,647 A | | 8/1986 | Lavielle et al. |
| 4,618,692 A | | 10/1986 | Scheffler et al. |
| 4,684,742 A | | 8/1987 | Stec et al. |
| 4,757,141 A | * | 7/1988 | Fung et al. |
| 6,420,586 B1 | * | 7/2002 | Hanson et al. |

FOREIGN PATENT DOCUMENTS

| | | |
|---|---|---|
| FR | 2 567 129 | 1/1986 |
| WO | WO 98/08853 | 3/1998 |
| WO | WO 00/52015 | 9/2000 |
| WO | WO 01/60820 A2 | 8/2001 |
| WO | WO 02/06293 A1 | 1/2002 |
| WO | WO 02/14344 A2 | 2/2002 |

* cited by examiner

Primary Examiner—Deborah C. Lambkin
(74) Attorney, Agent, or Firm—Birch, Stewart, Kolasch & Birch, LLP

(57) ABSTRACT

Novel compounds according to formula I

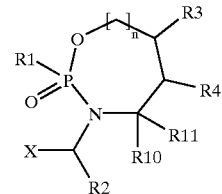

[I]

n is 0, 1, 2 or 3;

X represents hydroxamic acid (CONHOH), carboxylic acid, phosphonic acid, acetylthiomethyl group or a mercaptomethyl group; R2, R10 and R11 independently represent hydrogen or $(C_{1-8})$alkyl, $(C_{2-6})$alkenyl, $(C_{3-8})$cycloalkyl, aryl$(C_{0-6})$alkyl or heteroaryl$(C_{0-6})$alkyl, all of which may optionally be substituted; R3 and R4 independently represent hydrogen, hydroxy or alkoxy; provided that if A, A', Z and R5 are all bonds, and s and t are both 0 (zero), then R6 is different from hydrogen, and that at least one of R3, R4, R10 and R11 is different from hydrogen;

or a salt, hydrate or solvate thereof; pharmaceutical compositions comprising said compound; therapeutical methods comprising administering said compounds; and the use of said compounds in the manufacture of medicaments.

17 Claims, No Drawings

MMP INHIBITORS

This application claims benefit of Provisional No. 60/349,229 filed Jan. 18, 2002.

FIELD OF THE INVENTION

The invention relates to a hitherto unknown class of compounds, namely substituted 1,3,2 oxazaphosphacycloalkane derivatives, which exhibit matrix metalloprotease inhibitory effects, to pharmaceutical compositions comprising said compounds and to the use of said compounds in the manufacture of medicaments.

BACKGROUND OF THE INVENTION

The matrix metalloproteases (MMP) are a family of zinc containing enzymes capable of breaking down many protenaceous compounds in the extracellular matrix, such as collagen, gelatine, fibronectin, laminin and proteoglucan core protein.

There are at least 23 different MMPs classified according to their domain structure and substrate preferences [Lauer-Fields, *Exp.Opin.Ther.Patents*, 10, 1873–1884, 2000]. MMP may be classified into four main groups: Collagenases degrade fibrilar collagen; stromelysin degrade proteoglucans and glucoproteins; gelatinases degrade non-fibrilar and degraded collagen, i.e. gelatine; and finally the membrane bound MMPs [O'Brien, *J.Med.Chem.*, 43, 156–166, 2000]. The MMPs share a common multidomain structure, but are glycosylated at different sites and to different extent. All MMPs also share a common zinc-binding motif, HisGluXaaGlyHis, and the differences comprise the presence or absence of structural domains controlling such factors as substrate specificity, inhibitor binding, matrix binding and cell-surface localisation. The nomenclature for MMP is simple as they are named MMP-n, wherein n is an integer starting from 1.

MMP plays an important physiological role in tissue remodelling in normal tissue, e.g. angiogenesis, wound healing, bone resorption, ovulation and embryonic development. In healthy tissue, the activity of MMP is carefully controlled by gene expression, by synthesis of the enzymes in a latent pro-enzyme form, and by co-expression of endogenous tissue inhibitors of MMP (TIMP). Excessive or poorly regulated MMP activity has been implicated in a host of pathological conditions, and there has thus been a large effort to design drugs with MMP inhibitor effects, which could be used to re-establish control of the MMP activity.

Many known MMP inhibitors are peptide derivatives, based on naturally occurring amino acids, and with structural similarities to the cleavage sites in the natural substrates of MMP. Other known MMP inhibitors have less peptidic structure, and may be classified as pseudopeptides or peptidomimetics, e.g. sulfonamides.

Prior art of MMP inhibitors consists of peptidic structures [WO 95/19965 and WO 95/19956]; linear and cyclic sulfonamide compounds, [WO 97/44315, WO 00/09485 and EP 0979 816] and buturic and pentanoic acid derivatives [WO 97/43237, WO 97/43239 and WO 99/61413].

SUMMARY OF THE INVENTION

It has surprisingly been found that the novel substituted oxazaphosphacycloalkane derivatives of formula I are potent matrix metalloprotease inhibitors. Accordingly, the invention relates to compounds of formula I

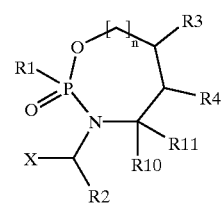

[I]

n is 0, 1, 2 or 3;

X represents hydroxamic acid (CONHOH), carboxylic acid, phosphonic acid, acetylthiomethyl group or a mercaptomethyl group;

R1 is

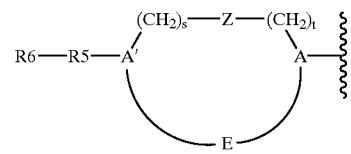

wherein E, when present, represents a bond or optionally substituted methylene or ethylene;

s and t are independently 0, 1, 2 or 3;

A and A' independently represent a bond, or a saturated or unsaturated, optionally substituted cyclic or heterocyclic hydrocarbon di- or triradical;

Z represents a bond, O, S, C(O), C(O)NR7, NR7C(O) or NR7, wherein R7 is hydrogen, hydroxy, branched or straight, saturated or unsaturated, optionally substituted hydrocarbon radical;

R5 represents a bond, alkane or alkene diradical, one or more ether diradicals (R—O—R') or amine diradicals (R—N—R'), wherein R and R' independently represent alkane or alkene diradicals with a C-content from 0 to 3;

R6 represents hydrogen, hydroxy, halogen, cyano, nitro, branched or straight, saturated or unsaturated, optionally substituted hydrocarbon radical, unsaturated optionally substituted cyclic or heterocyclic hydrocarbon radical, NR8R9, C(O)NR8R9, C(O)R8, CO(O)R8, S(O)$_2$R9, wherein each R8 and R9 independently represent hydrogen, halogen, a branched or straight, saturated or unsaturated, optionally substituted hydrocarbon radical;

R2, R10 and R11 independently represent hydrogen or (C$_{1-8}$)alkyl, (C$_{2-6}$)alkenyl, (C$_{3-8}$)cycloalkyl, aryl(C$_{0-6}$)alkyl or heteroaryl(C$_{0-6}$)alkyl, all of which may optionally be substituted;

R3 and R4 independently represent hydrogen, hydroxy or alkoxy;

provided that if A, A', Z and R5 are all bonds, and s and t are both 0 (zero), then R6 is different from hydrogen, and that at least one of R3, R4, R10 and R11 is different from hydrogen;

and a pharmaceutically acceptable salt, hydrate or solvate thereof.

The invention also relates to pharmaceutical compositions comprising compounds of formula I, to therapeutical treatments comprising administration to a patient of compounds according to formula I, and to the use of compounds according to formula I in the manufacture of medicaments.

The invention also relates to therapeutic methods involving the administration to a subject in need thereof an effective amount of a compound according to formula I.

Furthermore, the invention also provides compounds useful in the manufacture of compounds of formula I, i.e. compounds according to formula III and VII

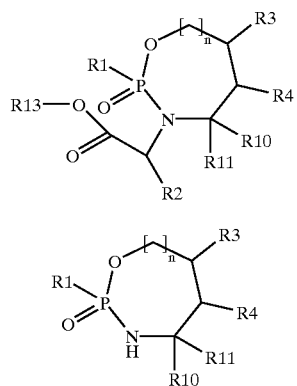

wherein R1, R2, R3, R4, R10, R11 and n have the same meaning as indicated above, and wherein R13 represents alkyl.

DETAILED DESCRIPTION OF THE INVENTION

As used in the specification, unless specified to the contrary, the following terms have the meaning indicated:

"Alkyl" refers to a straight or branched alkyl moiety, consisting solely of carbon and hydrogen, containing no unsaturation, Alkyl preferably has 1–12 carbon atoms, such as 1–6 carbon atoms. Examples include methyl, n-propyl, isobutyl, t-butyl, hexyl and dodecyl.

"$(C_2-C_6)$alkenyl" refers to a straight or branched alkenyl moiety having 2 to 6 carbon atoms having at least one double bond of either E or Z stereochemistry where applicable. This term includes, for example, vinyl, allyl, 1- and 2-butenyl and 2-methyl-2-propenyl.

The term "alkoxy" is intended to indicate a radical of formula OR, wherein R is alkyl as defined above, e.g. methoxy, ethoxy, propoxy, butoxy, etc.

The term "alkoxycarbonyl" is intended to indicate a radical of formula —COOR wherein R is alkyl as defined above, e.g. methoxycarbonyl, ethoxycabonyl, n-propoxycarbonyl, isopropoxycarbonyl, etc.

The term "saturated cyclic hydrocarbon" is intended to indicate cyclic compounds, optionally fused bicyclic rings, containing hydrogen and carbon, which are saturated, such as cyclopropane, cyclobutane, cyclopentane, cyclohexane, cycloheptane, cyclooctane, hydrindane and decaline.

The term "unsaturated cyclic hydrocarbon" is intended to indicate cyclic compounds, optionally fused bicyclic rings, containing hydrogen and carbon, in which one or more carbon-carbon bond is unsaturated, such as cyclopentene, cyclohexene, cyclohexadiene, cycloheptene, benzene, naphtene and 1,4-dihydronaphtene, indane and indene.

The term "heterocyclic hydrocarbon" is intended to indicate saturated or unsaturated cyclic compounds of hydrogen, carbon, and one or more heteroatoms selected from O, S, N and P, such as pyrrole, furan, thiophene, imidazole, oxazole, thiazole, pyrazole, pyrrolidine, pyridine, pyrimidine, tetrahydrotiophene, tetrahydrofuran, piperidine, piperazine, phosphalane, phosphorinane and phosporepane.

"Aryl" refers to phenyl or naphtyl.

"Cycloalkyl" means a saturated alicyclic moiety having from 3–8 carbon atoms and includes, for example, cyclopropyl, cyclopentyl, cyclohexyl, and cyclooctyl.

"Heteroaryl" refers to furanyl, pyridyl, indolyl, thienyl or imidazolyl.

The term halogen refers to members of the seventh main group in the periodic table, i.e. fluorine, chlorine, bromine and iodine.

Unless otherwise specified in the context in which it occurs, the term "substituted" as applied to any moiety herein means substituted with up to four substituents, each of which independently may be a $(C_{1-6})$alkoxy, $(C_{1-6})$alkyl, phenyl, hydroxy, thio, $(C_{1-6})$alkylthio, amino, halogen, cyano, cyanomethyl, trifluoromethyl, nitro, carboxy, —$CONH_2$, haloalkyl, alkylamino, hydroxyalkyl, alkylcarbonyl, —CONHR12 or —CONR12R12 wherein R12 is a $(C_1-C_6)$alkyl group or the residue of a natural α-amino acid.

Pharmaceutically acceptable salts of the compounds of the invention can be formed with bases. Such salts include salts derived from inorganic or organic bases, for example metal salts such as sodium or potassium salts, alkaline earth metal salts such as magnesium or calcium salts, and organic amine salts such as morpholine, piperidine, dimethylamine or diethylamine salts. If the compounds of the invention contain basic moieties, salts may also be formed with pharmaceutically acceptable inorganic or organic acids, such as hydrochloric, hydrobromic, and hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, maleic acid, these examples being considered as non-limiting for the invention.

There are chiral centres in the compounds according to the invention due to the presence of an asymmetric phosphorous atom and possibly one or more asymmetric carbon atoms. Likewise, any occurrence of carbon-carbon double bonds give rise to the presence of geometric isomers. The presence of more than one chiral centre gives rise to a number of diastereoisomers with R or S stereochemistry at each chiral centre. Formula I, and unless specified otherwise, all other formulae in this specification are to be understood to include all such isomers, in pure form, or as mixtures thereof.

Preferred compounds of the invention are those wherein the C-atom carrying the R2 group has R configuration.

Preferred compounds according to formula (I) are those in which X represents CONHOH. In particular preferred in this embodiment are those compounds of formula I wherein X represents CONHOH and n represents 0 or 1.

In a preferred embodiment, R1 is selected from the group consisting of alkoxyphenyl or phenoxyphenyl optionally substituted with halogen; halogen substituted hydrocarbon radical; cyano; phenylalkyl or naphtylalkyl optionally substituted with halogen; phenyl optionally substituted with halogen or nitro; hydrocarbon radical; biphenyl optionally substituted with halogen; benzylphenoxyl, phenyl-(NH)—C(O)-phenyl optionally substituted with halogen or cyano; and methoxy. Examples of particular R1 groups include 4-methoxyphenyl, 4-(4-chloro-phenoxy)-phenyl, 4-(4-bromophenoxy)-phenyl, 4-(4-trifluoromethylphenoxy)-phenyl, 4'bromo-4-biphenylyl, N-(4-chlorbenzoyl)-4-aminophenyl, 4-nitrophenyl, N-benzoyl-4-aminophenyl, 4-phenoxyphenyl.

In a further preferred embodiment, R2 is selected from the group consisting of hydrogen, $(C_{1-8})$alkyl, $(C_{2-6})$alkenyl and aryl($C_{0-6}$)alkyl. Examples of particular R2 groups include hydrogen, isopropyl, allyl, isobutyl, n-butyl, n-octyl and benzyl.

In a further preferred embodiment, R3 and R4 are independently methoxy or hydrogen.

In a still further preferred embodiment, R10 represents alkyl or optionally substituted phenyl or alkoxyphenyl. Particular examples of R10 are phenyl, 4-halo-phenyl and in particular 4-chloro-phenyl, 4-methoxyphenyl, methyl, isopropyl and isobutyl.

In a still further preferred embodiment, R11 represents hydrogen or alkyl, and in particular methyl.

Examples of compounds of formula I are:

(±)-2-(4-Methoxyphenyl)-2-oxo-4-phenyl-1,3,2-oxazaphosphorinane-3-acetohydroxamic acid (diastereomer 1),
(±)-2-(4-Methoxyphenyl)-2-oxo-4-phenyl-1,3,2-oxazaphosphorinane-3-acetohydroxamic acid (diastereomer 2),
(±)-2-[4-(4-Chlorophenoxy)-phenyl]-2-oxo-4-phenyl-1,3,2-oxazaphosphorinane-3-acetohydroxamic acid (diastereomer 1),
(±)-2-[4-(4-Chlorophenoxy)-phenyl]-2-oxo-4-phenyl-1,3,2-oxazaphosphorinane-3-acetohydroxamic acid (diastereomer 2),
(±)-2,4-Diphenyl-2-oxo-1,3,2-oxazaphosphorinane-3-acetohydroxamic acid (diastereomer 1),
(±)-2,4-Diphenyl-2-oxo-1,3,2-oxazaphosphorinane-3-acetohydroxamic acid (diastereomer 2),
(±)-2-[4-(4-Chlorophenoxy)-phenyl]-4-(4-methoxyphenyl)-2-oxo-1,3,2-oxazaphosphorinane-3-acetohydroxamic acid (diastereomer 1),
(±)-2-[4-(4-Chlorophenoxy)-phenyl]-4-(4-methoxyphenyl)-2-oxo-1,3,2-
(±)-2,4-Bis(4-methoxyphenyl)-2-oxo-1,3,2-oxazaphosphorinane-3-acetohydroxamic acid (diastereomer 1),
(±)-2,4-Bis(4-methoxyphenyl)-2-oxo-1,3,2-oxazaphosphorinane-3-acetohydroxamic acid (diastereomer 2),
(±)-2-(4-Methoxyphenyl)-4-(1-methylethyl)-2-oxo-1,3,2-oxazaphosphorepane-3-acetohydroxamic acid (diastereomer 2),
(±)-2-[4-(4-Chlorophenoxy)-phenyl]-4-(1-methylethyl)-2-oxo-1,3,2-oxazaphosphorepane-3-acetohydroxamic acid (diastereomer 1),
(±)-2-[4-(4-Chlorophenoxy)-phenyl]-4-(1-methylethyl)-2-oxo-1,3,2-oxazaphosphorepane-3-acetohydroxamic acid (diastereomer 2),
(±)-2-(4-Methoxyphenyl)-4-(2-methylpropyl)-2-oxo-1,3,2-oxazaphosphorepane-3-acetohydroxamic acid (diastereomer 2),
(±)-2-[4-(4-Chlorophenoxy)-phenyl]-4-(2-methylpropyl)-2-oxo-1,3,2-oxazaphosphorepane-3-acetohydroxamic acid (diastereomer 1),
(±)-2-[4-(4-Chlorophenoxy)-phenyl]-4-(2-methylpropyl)-2-oxo-1,3,2-oxazaphosphorepane-3-acetohydroxamic acid (diastereomer 2),
(±)2-[4-(4-Chlorophenoxy)-phenyl]-4,4-dimethyl-2-oxo-1,3,2-oxazaphosphorepane-3-acetohydroxamic acid,
(±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 1),
(±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 2),
(±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 3),
(±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 4)
(±)-4-(4-Chlorophenyl)-6-methoxy-2-(4-methoxyphenyl)-2-oxo-1,3,2-oxazaphosphorepane-3-acetohydroxamic acid (diastereomer 1),
(±)-4-(4-Chlorophenyl)-6-methoxy-2-(4-methoxyphenyl)-2-oxo-1,3,2-oxazaphosphorepane-3-acetohydroxamic acid (diastereomer 2),
(±)-4-(4-Chlorophenyl)-6-methoxy-2-(4-methoxyphenyl)-2-oxo-1,3,2-oxazaphosphorepane-3-acetohydroxamic acid (diastereomer 3),
(±)-4-(4-Chlorophenyl)-6-methoxy-2-(4-methoxyphenyl)-2-oxo-1,3,2-oxazaphosphorepane-3-acetohydroxamic acid (diastereomer 4),
(±)2-[4-(4-Chlorophenoxy)-phenyl]-4-phenyl-2-oxo-1,3,2-oxazaphosphorepane-3-acetohydroxamic acid (diastreomer 1),
(±)2-[4-(4-Chlorophenoxy)-phenyl]-4-phenyl-2-oxo-1,3,2-oxazaphosphorepane-3-acetohydroxamic acid (diastereomer 2),
(±)-2-(4-Methoxyphenyl)-4-methyl-2-oxo-1,3,2-oxazaphosphorepane-3-acetohydroxamic acid (mixture of 4 isomers),
(±)-2-[4-(4-Chlorophenoxy)-phenyl]-4-methyl-2-oxo-1,3,2-oxazaphosphorepane-3-acetohydroxamic acid (mixture of 4 isomers),
(±)-4-(4-Chlorophenylmethyl)-2-(4-methoxyphenyl)-2-oxo-1,3,2-oxazaphosphorepane-3-acetohydroxamic acid (mixture of 4 isomers)
(±)-4-(4-Chlorophenylmethyl)-2-[4-(4-chlorophenoxy)-phenyl]-2-oxo-1,3,2-oxazaphosphorepane-3-acetohydroxamic acid (mixture of 4 isomers),
(±)-2-[4-(4-chlorophenoxy)-phenyl]-4-(2-furanyl)-6-methoxy-2-oxo-1,3,2-oxazaphosphorepane-3-acetohydroxamic acid (diastereomer 2),
(±)-2-[4-(4-chlorophenoxy)-phenyl]-5-hydroxy-2-oxo-1,3,2-oxazaphosphorepane-3-acetohydroxamic acid (diastereomer 1),
(±)-2-[4-(4-chlorophenoxy)-phenyl]-5-hydroxy-2-oxo-1,3,2-oxazaphosphorepane-3-acetohydroxamic acid (diastereomer 2);

and the corresponding carboxylic acids.

Examples of compounds according to formula III and VII are (±)-2-(4-Methoxyphenyl)-2-oxo-4-phenyl-1,3,2-oxazaphosphorinane (diastereomer 1),
(±)-2-(4-Methoxyphenyl)-2-oxo-4-phenyl-1,3,2-oxazaphosphorinane (diastereomer 2),
(±)-2-[4-(4-Chlorophenoxy)-phenyl]-2-oxo-4-phenyl-1,3,2-oxazaphosphorinane (diastereomer 1),
(±)-2-[4-(4-Chlorophenoxy)-phenyl]-2-oxo-4-phenyl-1,3,2-oxazaphosphorinane (diastereomer 2),
(±)-2,4-Diphenyl-2-oxo-1,3,2-oxazaphosphorinane (diastereomer 1),
(±)-2,4-Diphenyl-2-oxo-1,3,2-oxazaphosphorinane (diastereomer 2),
(±)-2-[4-(4-Chlorophenoxy)-phenyl]-4-(4-methoxyphenyl)-2-oxo-1,3,2-oxazaphosphorinane (diastereomer 1),
(±)-2-[4-(4-Chlorophenoxy)-phenyl]-4-(4-methoxyphenyl)-2-oxo-1,3,2-oxazaphosphorinane (diastereomer 2),
(±)-2,4-Bis(4-methoxyphenyl)-2-oxo-1,3,2-oxazaphosphorinane (diastereomer 1), (±)-2,4-Bis(4-methoxyphenyl)-2-oxo-1,3,2-oxazaphosphorinane (diastereomer 2),
(±)-2-(4-Methoxyphenyl)-4-(1-methylethyl)-2-oxo-1,3,2-oxazaphosphorepane (diastereomer 1),
(±)-2-(4-Methoxyphenyl)-4-(1-methylethyl)-2-oxo-1,3,2-oxazaphosphorepane (diastereomer 2),
(±)-2-[4-(4-Chlorophenoxy)-phenyl]-4-(1-methylethyl)-2-oxo-1,3,2-oxazaphosphorepane (mixture of 4 isomers),
(±)-2-(4-Methoxyphenyl)-4-(2-methylpropyl)-2-oxo-1,3,2-oxazaphosphorepane (mixture of 4 isomers),
(±)-2-[4-(4-Chlorophenoxy)-phenyl]-4-(2-methylpropyl)-2-oxo-1,3,2-oxazaphosphorepane (mixture of 4 isomers),
(±)-2-[4-(4-Chlorophenoxy)-phenyl]-4,4-dimethyl-2-oxo-1,3,2-oxazaphosphorepane,
(±)-4-(4-Chlorophenyl)-2-[4-(4-chlorophenoxy)-phenyl]-6-methoxy-2-oxo-1,3,2-oxazaphosphorepane (diastereomer 1),
(±)-4-(4-Chlorophenyl)-2-[4-(4-chlorophenoxy)-phenyl]-6-methoxy-2-oxo-1,3,2-oxazaphosphorepane (diastereomer 2),
(±)-4-(4-Chlorophenyl)-2-[4-(4-chlorophenoxy)-phenyl]-6-methoxy-2-oxo-1,3,2-oxazaphosphorepane (diastereomer 3),
(±)-4-(4-Chlorophenyl)-2-[4-(4-chlorophenoxy)-phenyl]-6-methoxy-2-oxo-1,3,2-oxazaphosphorepane (diastereomer 4),
(±)-4-(4-Chlorophenyl)-2-(4-methoxyphenyl)-6-methoxy-2-oxo-1,3,2-oxazaphosphorepane (diastereomer 1),
(±)-4-(4-Chlorophenyl)-2-(4-methoxyphenyl)-6-methoxy-2-oxo-1,3,2-oxazaphosphorepane (diastereomer 2),
(±)-4-(4-Chlorophenyl)-2-(4-methoxyphenyl)-6-methoxy-2-oxo-1,3,2-oxazaphosphorepane (diastereomer 3),
(±)-4-(4-Chlorophenyl)-2-(4-methoxyphenyl)-6-methoxy-2-oxo-1,3,2-oxazaphosphorepane (diastereomer 4),
(±)-2-[4-(4-Chlorophenoxy)-phenyl]-4-phenyl-2-oxo-1,3,2-oxazaphosphorepane (diastereomer 1),
(±)-2-[4-(4-Chlorophenoxy)-phenyl]-4-phenyl-2-oxo-1,3,2-oxazaphosphorepane (diastereomer 2),
(±)-2-[4-(4-chlorophenoxy)-phenyl]-4-(2-furanyl)-6-methoxy-2-oxo-1,3,2-oxazaphosphorepane (diastereomer 1),
(±)-2-[4-(4-chlorophenoxy)-phenyl]-4-(2-furanyl)-6-methoxy-2-oxo-1,3,2-oxazaphosphorepane (diastereomer 2),
(±)-2-[4-(4-chlorophenoxy)-phenyl]-5-[tert-butyldimethylsilyloxy]-2-oxo-1,3,2-oxazaphosphorepane (diastereomer 1),
(±)-2-[4-(4-chlorophenoxy)-phenyl]-5-[tert-butyldimethylsilyloxy]-2-oxo-1,3,2-oxazaphosphorepane (diastereomer 2),
(±)-Ethyl 2-(4-Methoxyphenyl)-2-oxo-4-phenyl-1,3,2-oxazaphosphorinane-3-acetate (diastereomer 1),
(±)-Ethyl 2-(4-Methoxyphenyl)-2-oxo-4-phenyl-1,3,2-oxazaphosphorinane-3-acetate (diastereomer 2),
(±)-Ethyl 2-[4-(4-Chlorophenoxy)-phenyl]-2-oxo-4-phenyl-1,3,2-oxazaphosphorinane-3-acetate (diastereomer 1),
(±)-Ethyl 2-[4-(4-Chlorophenoxy)-phenyl]-2-oxo-4-phenyl-1,3,2-oxazaphosphorinane-3-acetate (diastereomer 2),
(±)-Ethyl 2,4-Diphenyl-2-oxo-1,3,2-oxazaphosphorinane-3-acetate (diastereomer 1),
(±)-Ethyl 2,4-Diphenyl-2-oxo-1,3,2-oxazaphosphorinane-3-acetate (diastereomer 2),
(±)-Ethyl 2-[4-(4-Chlorophenoxy)-phenyl]-4-(4-methoxyphenyl)-2-oxo-1,3,2-oxazaphosphorinane-3-acetate (diastereomer 1),
(±)-Ethyl 2-[4-(4-Chlorophenoxy)-phenyl]-4-(4-methoxyphenyl)-2-oxo-1,3,2-oxazaphosphorinane-3-acetate (diastereomer 2),
(±)-Ethyl 2,4-Bis(4-Methoxyphenyl)-2-oxo-1,3,2-oxazaphosphorinane-3-acetate (diastereomer 1),
(±)-Ethyl 2,4-Bis(4-Methoxyphenyl)-2-oxo-1,3,2-oxazaphosphorinane-3-acetate (diastereomer 2),
(±)-Ethyl 2-(4-Methoxyphenyl)-4-(1-methylethyl)-2-oxo-1,3,2-oxazaphosphorepane-3-acetate (diastereomer 1),
(±)-Ethyl 2-(4-Methoxyphenyl)-4-(1-methylethyl)-2-oxo-1,3,2-oxazaphosphorepane-3-acetate (diastereomer 2),
(±)-Ethyl 2-[4-(4-Chlorophenoxy)-phenyl]-4-(1-methylethyl)-2-oxo-1,3,2-oxazaphosphorepane-3-acetate (diastereomer 1),
(±)-Ethyl 2-(4-Methoxyphenyl)-4-(2-methylpropyl)-2-oxo-1,3,2-oxazaphosphorepane-3-acetate (diastereomer 2),
(±)-Ethyl 2-(4-Methoxyphenyl)-4-(2-methylpropyl)-2-oxo-1,3,2-oxazaphosphorepane-3-acetate (diastereomer 1),
(±)-Ethyl 2-[4-(4-Chlorophenoxy)-phenyl]-4-(2-methylpropyl)-2-oxo-1,3,2-oxazaphosphorepane-3-acetate (mixture of 4 isomers),
(±)-Ethyl 2-[4-(4-Chlorophenoxy)-phenyl]-4,4-dimethyl-2-oxo-1,3,2-oxazaphosphorepane-3-acetate,
(±)-Ethyl 4-(4-Chlorophenyl)-2-[4-(4-chlorophenoxy)-phenyl]-6-methoxy-2-oxo-1,3,2-oxazaphosphorepane-3-acetate (diastereomer 1),
(±)-Ethyl 4-(4-Chlorophenyl)-2-[4-(4-chlorophenoxy)-phenyl]-6-methoxy-2-oxo-1,3,2-oxazaphosphorepane-3-acetate (diastereomer 2),
(±)-Ethyl 4-(4-Chlorophenyl)-2-[4-(4-chlorophenoxy)-phenyl]-6-methoxy-2-oxo-1,3,2-oxazaphosphorepane-3-acetate (diastereomer 3),
(±)-Ethyl 4-(4-Chlorophenyl)-2-[4-(4-chlorophenoxy)-phenyl]-6-methoxy-2-oxo-1,3,2-oxazaphosphorepane-3-acetate (diastereomer 4),
(±)-Ethyl 4-(4-Chlorophenyl)-6-methoxy-2-(4-methoxyphenyl)-2-oxo-1,3,2-oxazaphosphorepane-3-acetate (diastereomer 1),
(±)-Ethyl 4-(4-Chlorophenyl)-6-methoxy-2-(4-methoxyphenyl)-2-oxo-1,3,2-oxazaphosphorepane-3-acetate (diastereomer 2),
(±)-Ethyl 4-(4-Chlorophenyl)-6-methoxy-2-(4-methoxyphenyl)-2-oxo-1,3,2-oxazaphosphorepane-3-acetate (diastereomer 3),
(±)-Ethyl 4-(4-Chlorophenyl)-6-methoxy-2-(4-methoxyphenyl)-2-oxo-1,3,2-oxazaphosphorepane-3-acetate (diastereomer 4),
(±)-Ethyl 2-[4-(4-Chlorophenoxy)-phenyl]-4-phenyl-2-oxo-1,3,2-oxazaphosphorepane-3-acetate (diastereomer 1),
(±)-Ethyl 2-[4-(4-Chlorophenoxy)-phenyl]-4-phenyl-2-oxo-1,3,2-oxazaphosphorepane-3-acetate (diastereomer 2),
(±)-Ethyl 2-(4-Methoxyphenyl)-4-methyl-2-oxo-1,3,2-oxazaphosphorepane-3-acetate (mixture of 4 isomers),
(±)-Ethyl 2-[4-(4-Chlorophenoxy)-phenyl]-4-methyl-2-oxo-1,3,2-oxazaphosphorepane-3-acetate (mixture of 4 isomers),
(±)-Ethyl 4-(4-Chlorophenylmethyl)-2-(4-methoxyphenyl)-2-oxo-1,3,2-oxazaphosphorepane-3-acetate (mixture of 4 isomers),
(±)-Ethyl 4-(4-Chlorophenylmethyl)-2-[4-(4-chlorophenoxy)-phenyl)]-2-oxo-1,3,2-oxazaphosphorepane-3-acetate (mixture of 4 isomers),
(±)-Ethyl 2-[4-(4-chlorophenoxy)-phenyl]-4-(2-furanyl)-6-methoxy-2-oxo-1,3,2-oxazaphosphorepane-3-acetate (diastereomer 1),
(±)-Ethyl 2-[4-(4-chlorophenoxy)-phenyl]-4-(2-furanyl)-6-methoxy-2-oxo-1,3,2-oxazaphosphorepane-3-acetate (diastereomer 2),
(±)-Ethyl 5-(tert-butyldimethylsilyloxy)-2-[4-(4-chlorophenoxy)-phenyl]-2-oxo-1,3,2-oxazaphosphorepane-3-acetate (diastereomer 1), (±)-Ethyl 5-(tert-butyldimethylsilyloxy)-2-[4-(4-chlorophenoxy)-phenyl]-2-oxo-1,3,2-oxazaphosphorepane-3-acetate (diastereomer 2), (±)-Ethyl 2-[4-(4-chlorophenoxy)-phenyl]-5-hydroxy-2-oxo-1,3,2-oxazaphosphorepane-3-acetate (diastereomer 2).

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formula (I) may be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula (I) falling into a given class may be compatible with some of the reaction conditions required in some of the methods described. Such restrictions to the substituents which are compatible with the reaction conditions will be readily apparent to one skilled in the art and alternative methods can be used.

Compounds according to the present invention in which X is a hydroxamic acid group —CONHOH may be prepared from compounds of the invention in which X is a carboxylic acid group —COOH. That process comprises reacting an acid of general formula (II) (in these and the following formulae R1, R2, R3, R4, R10, R11 and n have the above meanings unless otherwise specifically indicated; R13 represents an alkyl)

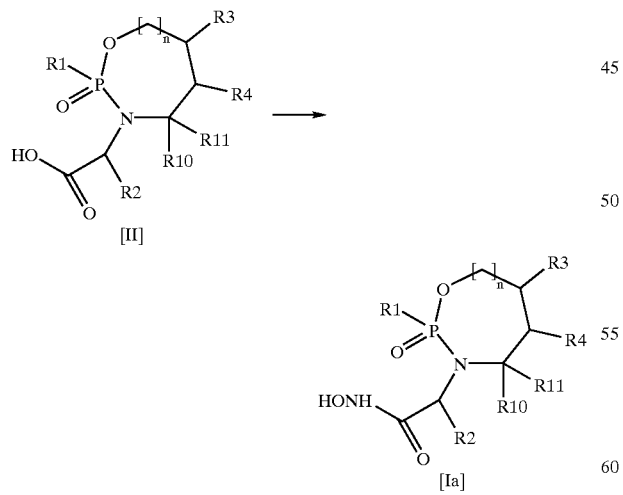

with hydroxylamine, O-protected hydroxylamine or N,O-diprotected hydroxylamine. Other substituents of the acids (II) may themselves be protected from such reaction, and the protecting groups may subsequently be removed from the resulting hydroxamic acid moiety.

The condensation is carried out using one of the many methods for the formation of amide bonds known to one skilled in the art of organic synthesis, e.g. the mixed carbonic anhydride (isobutyl chloroformate) method.

Compounds according to the present invention in which X is a hydroxamic acid group —CONHOH may also be prepared from esters of general formula (III). That process comprises reacting an ester of general formula (III) with hydroxylamine or O-protected hydroxylamine in the presence of a base.

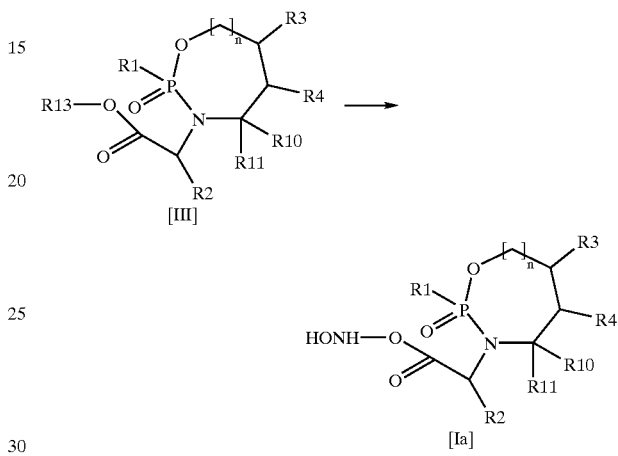

Compounds according to the present invention in which X is a carboxylic acid group —COOH may be prepared from esters of general formula (III) by basic hydrolysis.

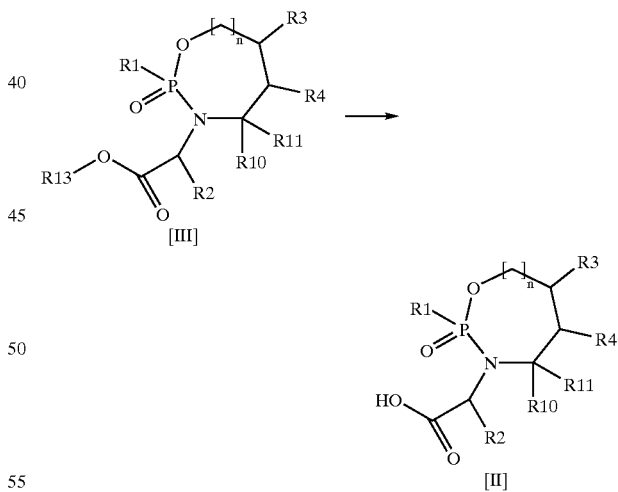

The esters of formula (III) may be prepared from phosphonyl dichlorides (IV) and amino alcohols (V) in the presence of a base.

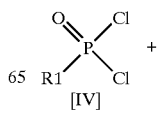

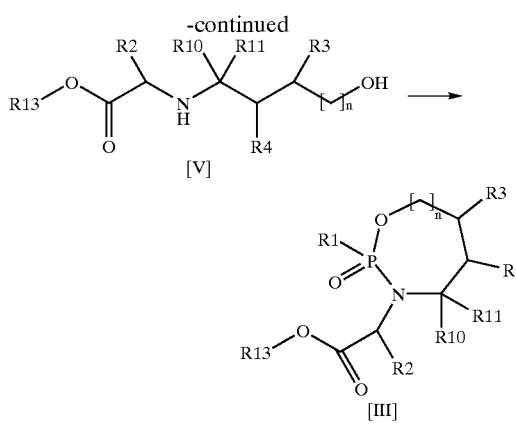

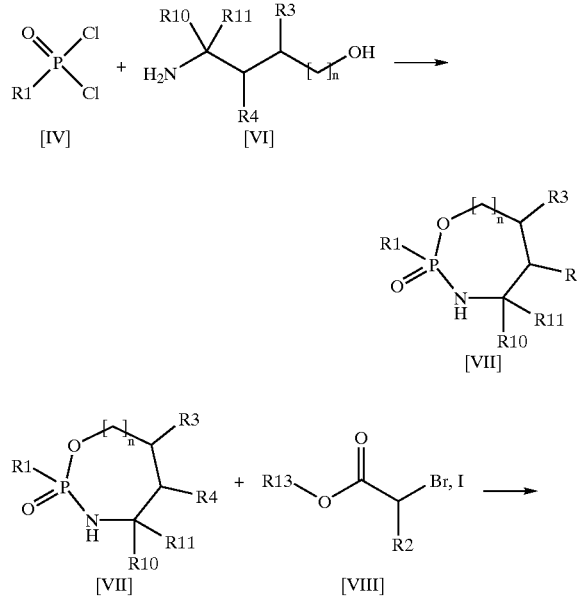

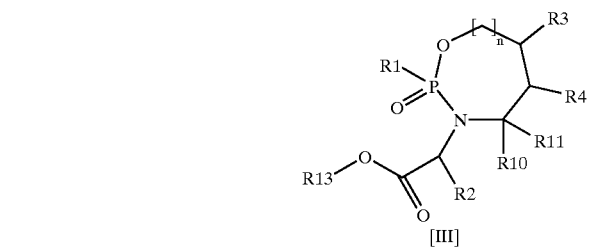

The esters of formula (III) may also be prepared from phosphonyl dichlorides (IV) and amino alcohols (VI) in the presence of a base and subsequent alkylation of the intermediate oxazaphosphacycloalkane (VII) utilising haloesters (VIII) in the presence of a base.

Starting materials (IV) are either commercially available or readily prepared from aryl bromides or aryl triflates by palladium catalysed phosphonation (Hirao et al., Synthesis, 56–57, 1981) followed by chlorination (H. Quast et al., Synthesis, 490, 1974 or N. N. Bhongle et al., Synthetic Communications, 17, 1071–76 (1987)).

Starting materials (V) are readily obtained e.g. by alkylation of aminoalkohols (VI) with haloesters (VIII). Aminoalcohols (V) in which R3 and R4 are hydrogen and in which n=1 or 2 may be prepared from homoallylic amino acid esters (J. Org. Chem., 59, 7766–7773 (1994)) by ozonolysis/reduction (n=1) or hydroboration/oxidation (n=2).

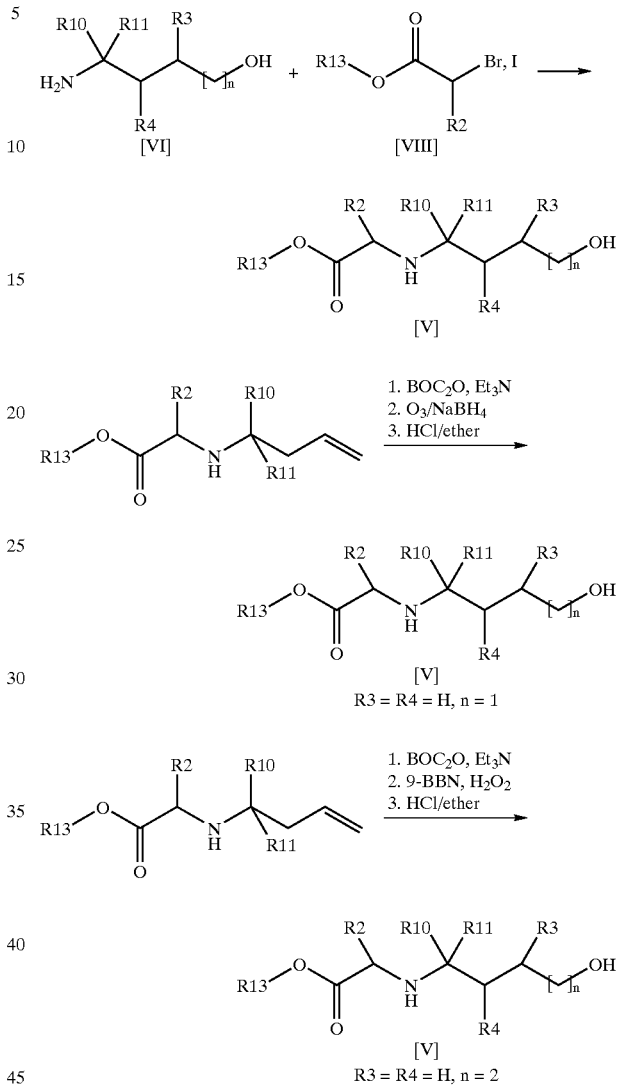

Starting materials (VI), in which R4 is hydrogen may be prepared using routine synthetic methods for instance in the following manner: Nitrones of general formula (IX) (prepared as described in Synth. Comm. 24(18), 2537–2550 (1994) or Synlett (5), 602–604 (1999)) may be heated in ω-alkenyl alcohols to give the isoxazolidines (X), which may subsequently be reduced by treatment with Zn-dust in acetic acid at 60° C. to yield aminodiols (XI). The primary alcohol may be protected using triisopropylsilylchloride and base, the amino-function may be protected using ditertbutyldicarbonate to yield compounds (XII). The secondary alcohol may then either be protected using e.g. acetic anhydride and base or alkylated using an alkylhalide and base, the benzyl group may be removed using 2,3-dichloro-5,6-dicyano-1,4-benzoquinone (DDQ) and the BOC and silyl-protecting groups may simultaneously be removed using HCl in ethanol at 60° C. to give compounds (VI), in which PG denotes either alkyl group or a protecting group to be removed at a later stage.

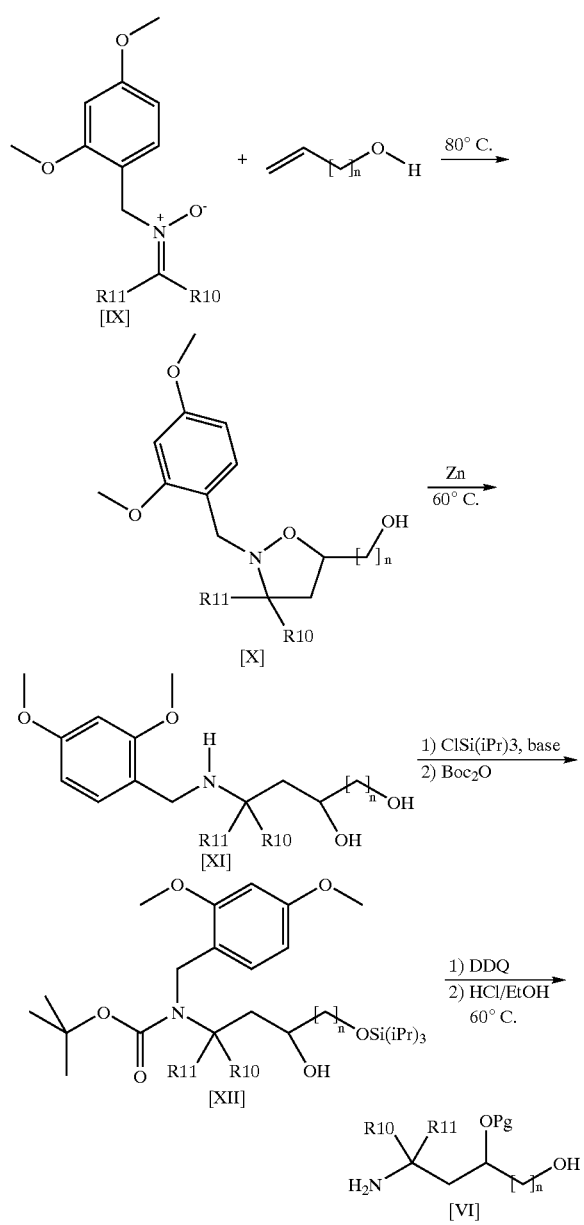

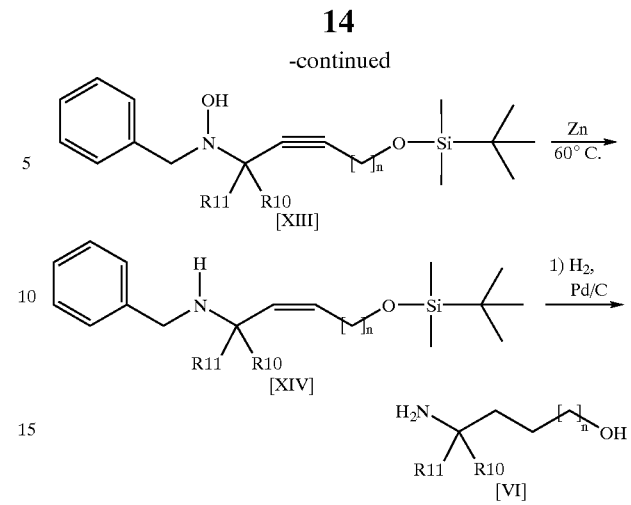

nitrones (IX) (prepared as described in Synlett (5), 602–604 (1999)) may be condensed with silylated alkynols (XX) in the presence of lithium diisopropylamine (LDA) at −70° C. The resulting hydroxylamines (XIII) may then be treated with Zn-dust in acetic acid/methanol to yield amines (XIV). Subsequent hydrogenation and treatment with HCl in ethanol may then afford amines (VI).

Alternatively, starting materials (VI) in which R3 and R4 are hydrogen with n=1 or 2 may be prepared from substituted 4-amino-1-butenes (J. Org. Chem., 59, 7766–7773, 1994) by standard ozonlysis/reduction (n=1) or by hydroboration/oxidation (n=2), with the amino group appropriately protected.

Starting materials (VI) in which R3 and R4 are hydroxy or alkoxy may be prepared from compounds (XIV) by dihydroxylation. The resulting alcohol functions may, if necessary, be alkylated using an alkylhalide and base after BOC protection of the amino group, and the benzyl, silyl and BOC protecting groups subsequently be removed as described for compounds (XIV).

Starting materials (VI) in which R4 is hydrogen may be prepared from compounds (XIV) by hydroboration/oxidation or by epoxidation followed by ring-opening of the epoxide using e.g. Red-Al. The resulting alcohol function may, if necessary, be alkylated using an alkylhalide and base after BOC protection of the amino group, and the benzyl, silyl and BOC protecting groups subsequently be removed as described for compounds (XIV).

Starting materials (VI) in which R4 is hydroxy or alkoxy, R3 is hydrogen and n=1 may be prepared from 4-benzyloxycarbonylamino-3-hydroxybutyric acid (XXI, Tetrahedron 50(47), 13347–68 (1994)) in the following manner:

Starting materials (VI) in which R4 is an hydroxy-group and R10, R11 and R3 are hydrogen are commercially available.

Starting materials (VI), in which R3 and R4 are hydrogen are either commercially available, known compounds or may be prepared using routine synthetic methods for instance in the following manner:

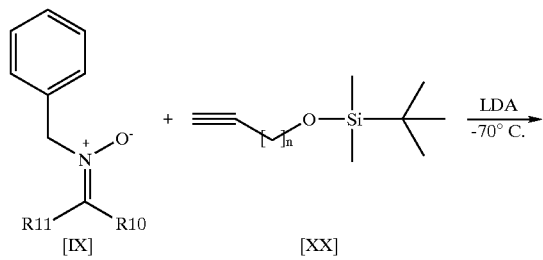

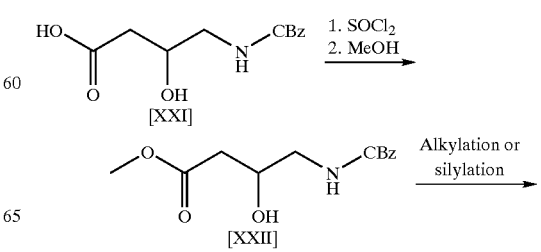

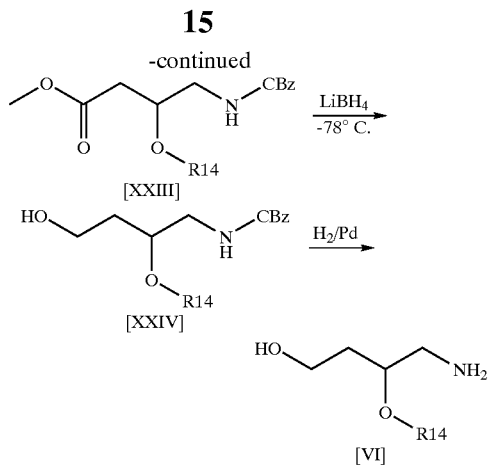

R14 represents an alkyl or a transient protecting group, such as a silyl group. Alkylation or silylation is carried out by standard synthetic methods. If R14 is a silyl, this group is cleaved after cyclisation of (VI) with a phosphonyl dichloride (IV).

Starting materials (VIII) containing bromine are either commercially available or easily prepared from the corresponding amino acids by standard synthetic methods (e.g. J.Org.Chem. 50(9), 1356–1359 (1985)) and subsequent esterification. Starting materials (VIII) containing iodine can be prepared by conversion of the bromoacetic acid esters (VIII) with sodium iodide.

Compounds (XVI) according to the present invention in which X is a phosphonic acid group —P(O)(OH)2 may be prepared by alkylation of oxazaphosphacycloalkanes (VII) with alkyl or silyl phosphonate halides (XV), in the presence of base, followed by deprotection. The deprotection of alkyl phosphonates is carried out by treatment with TMSI. Silyl phosphonates are readily converted to phosphonic acids by treatment with water. Alkyl phosphonate halides (XV) are commercially available or known compounds.

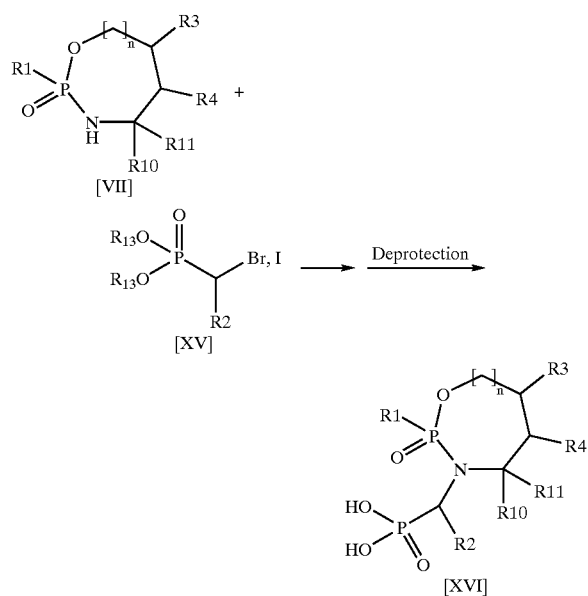

Compounds (XVIII) according to the present invention in which X is an acetylthiomethyl moiety —CH2SCOCH3 may be prepared by alkylation of oxazaphosphacycloalkanes (VII) with an acetylthioethyl halide (XVII) in the presence of base. Compounds (XIX) according to the present invention in which X is a mercaptomethyl —CH2SH group may prepared by removal of the acetyl group from compounds (XVIII) with aqueous base

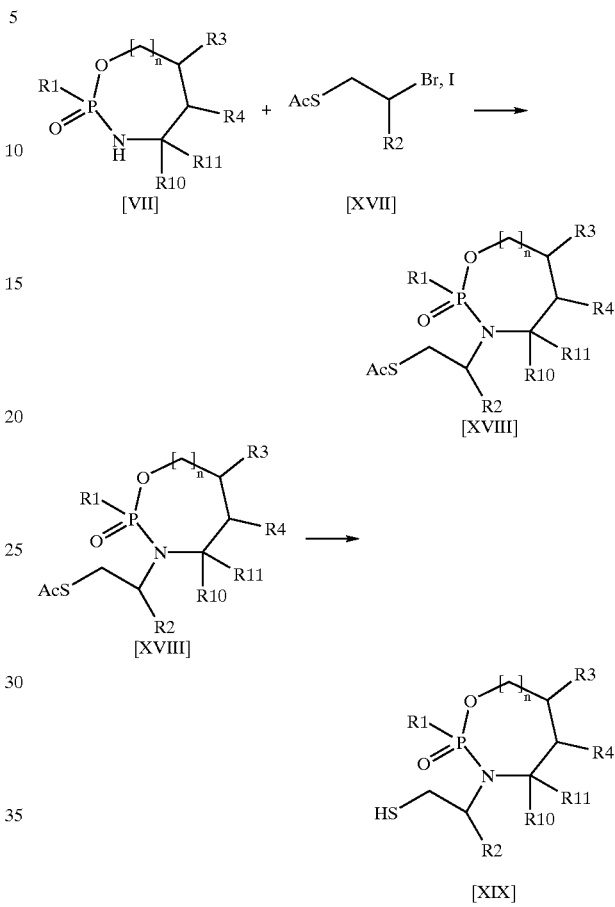

Preparation of pure isomeric compounds of the invention may be accomplished in one of the following ways:
1. Preparation of enantiomerically pure intermediates (V) or (VI) by enantioselective syntheses as described in J. Org. Chem. 59, 7766–7773, 1994. Furthermore, a few optically active amino alcohols VI are commercially available. Subsequent ring closure with phosphonyl dichlorides (IV) affords a pair of diastereoisomers that may be separated by chromatography.
2. Optical resolution of the racemic oxazacyclophosphane intermediates (VII) using chiral silyl chlorides according to the procedure described in J. Org. Chem. 43, 1111–1114 (1978).
3. Esterification of racemic carboxylic acid intermediates (II) with optically active alcohols such as (–)-menthol or (–)-N-methylephedrine, or amidation with optically active amines such as (–)-2-phenylglycinol or Evans' oxazolidinones. The resulting diastereoisomeric esters or amides may be separated by either crystallisation or by chromatography and hydrolysed to afford optically active carboxylic acids.
4. Resolution of diastereomeric salts formed from the racemic carboxylic acids (II) and optically active bases such as quinotoxine or cinchotoxine.
5. Resolution of the racemic oxazacyclophosphanes (VII) or esters (III) by chiral chromatography.

After the preparation of pure isomeric intermediates by any of the above methods, the intermediates may be transformed to compounds of formula I by the reactions described herein.

Imbalance in MMP production or activity has been implicated in many diseases, hence the therapeutic value of MMP inhibitors. Compounds that have the property of inhibiting MMP are thus believed to be potentially useful for treating, preventing and/or ameliorating disease severity, disease symptoms, and/or periodicity of reoccurrence of a disease or condition associated with an imbalance in MMP production or activity. Diseases or conditions include those involving tissue breakdown or inflammation, such as rheumatoid arthritis, osteoarthritis, osteopenias, such as osteroporosis, periodontitis, gingivitis, corneal epidermal, gastric ulceration, skin ageing, tumour metastasis, tumour invasion and tumour growth; diseases associated with neuroinflammatory disorder, including those involving myelin degradation, such as multiple sclerosis; angiogenesis dependent diseases, which include arthritic conditions and solid tumour growth, psoriasis, proliferative retinopathies, neovascular glaucoma, ocular tumours, angiofibromas and hemangiomas [Vu in *Metalloproteases*, Parks and Mecham (Eds.), 115–148, 1998, Academic Press; Mullins, *Biochem.Biophys.Acta*, 695, 117–214, 1983; Henderson, *Drugs of the Future*, 15, 495–508, 1990; Reich, *Cancer Res*, 48, 3307–3312, 1988; Whitaker, *Chem.Rev.*, 99, 2735–2776, 1999].

Moreover, MMP inhibitors are also potentially useful for treating, preventing and/or ameliorating disease severity, disease symptoms, and/or periodicity of reoccurrence of a disease or condition associated excess Tumour Necrosis Factor α (TNF-α) production [Whitaker, *Chem.Rev.*, 99, 2735–2776, 1999]. TNF-α is a potent proinflammatory cytokine which has been implicated in inflammatory diseases or conditions, arthritis, asthma, septic shock, fever, cardiovascular effects, haemorrage, coagulation, acute phase reponse, Crohn's disease, mycobacterial infection, meningitis, psoriasis, congestive heart failure and apoptosis. TNF-α is expressed in the cells as a membrane-bound 26 kDa protein, which is proteolytically cleaved to release a 17 kDa active, soluble form. The TNF-α processing is catalysed by the enzyme TNF-α convertase (TACE), which is a metalloprotease, and several MMP inhibitors have been found to inhibit TNF-α processing [Mohler, *Nature*, 370, 218, 1994]. Excess TNF-α production can thus potentially be controlled by treatment with an MMP inhibitor.

In another aspect, the invention relates to pharmaceutical formulations of a compound of formula I. The formulations of the present invention, both for veterinary and for human medical use, comprise active ingredients in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

Conveniently, the active ingredient comprises from 0.1–100% by weight of the formulation. Conveniently, dosage unit of a formulation contain between 0.07 mg and 1 g of a compound of formula I.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g as disclosed in Remington, *The Science and Practice of Pharmacy*, $20^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be may in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Tehcnology, vol.9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Tehcnology, vol.2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

Prodrugs of the present invention may also be delivered by use of monoclonale antibodies as individual carriers to which the compound molecules are coupled.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including antioxidants), emulsifying agents and the like.

In the systemic treatment using the present invention daily doses of from 0.001–500 mg per kilogram body weight, preferably from 0.002–100 mg/kg of mammal body weight, for example 0.003–20 mg/kg of a compound of formula I is administered, typically corresponding to a daily dose for an adult human of from 0.01 to 37000 mg. In the topical treatment of dermatological disorders, ointments, creams or lotions containing from 0.1–750 mg/g, and preferably from 0.1–500 mg/g, for example 0.1–200 mg/g of a compound of formula I is administered. For topical use in ophthalmology ointments, drops or gels containing from 0.1–750 mg/g, and preferably from 0.1–500 mg/g, for example 0.1–200 mg/g of a compound of formula I is administered. The oral compositions are formulated, preferably as tablets, capsules, or drops, containing from 0.07–1000 mg, preferably from 0.1–500 mg, of a compound of formula I per dosage unit.

The invention also includes incorporating other pharmacologically active ingredients, normally used in the treatment of the disease states mentioned above, into the formulation of the present invention. Such active ingredients may be anti-cancer drugs, such as chemotherapeutic agents, hormonal agents or biological response modifiers.

Administration to patients in need thereof of the compounds or compositions of the present invention is expected to be useful in the treatment of the above mentioned diseases.

GENERAL PROCEDURES, PREPARATIONS AND EXAMPLES

The exemplified compounds of formula Ia are listed in Table 4, exemplified compounds of general formula (II) in Table 3, intermediates of general formula (III) in Table 2, and intermediates of general formula (VII) in Table 1. Except if otherwise specified, the compounds are racemic.

All melting points are uncorrected. For $^1$H nuclear magnetic resonance (NMR) spectra (300 MHz) and $^{13}$C NMR (75.6 MHz) chemical shift values ($\delta$) (in ppm) are quoted, unless otherwise specified, for deuteriochloroform solutions relative to internal tetra-methylsilane ($\delta$=0.00) or chloroform ($\delta$=7.25) or deuteriochloroform ($\delta$=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. Mass spectra were recorded on a QUATTRO II (Micromass). The organic solvents used were anhydrous. Chromatography was performed on silica gel.

The following abbreviations have been used throughout:

BOC tertbutyloxycarbonyl
Cbz benzyloxycarbonyl
DDQ 2,3-dichloro-5,6-dicyano-1,4-benzoquinone
EtOAc ethyl acetate
LDA lithium diisopropylamine
MS Mass spectroscopy
NMM N-methylmorpholine
NMR Nuclear magnetic resonance
rt Room temperature
TBAF Tetrabutylammoniumfluoride
THF Tetrahydrofuran
TMSI Trimethylsilyliodid
ph phenyl

TABLE 1

Compounds of general formula (VII)

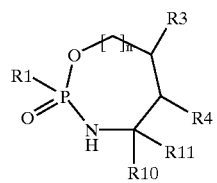

| Comp No. | Prep no. | R1 | R3 | R4 | R10 | R11 | n |
|---|---|---|---|---|---|---|---|
| 201a | 1 | 4-methoxy-phenyl | H | H | phenyl | H | 0 |
| 201b | 2 | 4-methoxy-phenyl | H | H | phenyl | H | 0 |
| 202a | 3 | 4-(4-Cl-phenoxy)-phenyl | H | H | phenyl | H | 0 |

TABLE 1-continued

Compounds of general formula (VII)

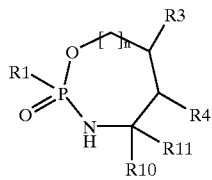

| Comp No. | Prep no. | R1 | R3 | R4 | R10 | R11 | n |
|---|---|---|---|---|---|---|---|
| 202b | 4 | 4-(4-Cl-phenoxy)-phenyl | H | H | phenyl | H | 0 |
| 203a | 5 | phenyl | H | H | phenyl | H | 0 |
| 203b | 6 | phenyl | H | H | phenyl | H | 0 |
| 204a | 7 | 4-(4-Cl-phenoxy)-phenyl | H | H | 4-methoxy-phenyl | H | 0 |
| 204b | 8 | 4-(4-Cl-phenoxy)-phenyl | H | H | 4-methoxy-phenyl | H | 0 |
| 205a | 9 | 4-methoxy-phenyl | H | H | 4-methoxy-phenyl | H | 0 |
| 205b | 10 | 4-methoxy-phenyl | H | H | 4-methoxy-phenyl | H | 0 |
| 206a | 11 | 4-methoxy-phenyl | H | H | isopropyl | H | 1 |
| 206b | 12 | 4-methoxy-phenyl | H | H | isopropyl | H | 1 |
| 207* | 13 | 4-(4-Cl-phenoxy)-phenyl | H | H | isopropyl | H | 1 |
| 208* | 14 | 4-methoxy-phenyl | H | H | isobutyl | H | 1 |
| 209* | 15 | 4-(4-Cl-phenoxy)-phenyl | H | H | isobutyl | H | 1 |
| 210 | 16 | 4-(4-Cl-phenoxy)-phenyl | H | H | methyl | methyl | 1 |
| 211a | 17 | 4-(4-Cl-phenoxy)-phenyl | methoxy | H | 4-Cl-phenyl | H | 1 |
| 211b | 18 | 4-(4-Cl-phenoxy)-phenyl | methoxy | H | 4-Cl-phenyl | H | 1 |
| 211c | 19 | 4-(4-Cl-phenoxy)-phenyl | methoxy | H | 4-Cl-phenyl | H | 1 |
| 211d | 20 | 4-(4-Cl-phenoxy)-phenyl | methoxy | H | 4-Cl-phenyl | H | 1 |
| 212a | 21 | 4-methoxy-phenyl | methoxy | H | 4-Cl-phenyl | H | 1 |
| 212b | 22 | 4-methoxy-phenyl | methoxy | H | 4-Cl-phenyl | H | 1 |
| 212c | 23 | 4-methoxy-phenyl | methoxy | H | 4-Cl-phenyl | H | 1 |
| 212d | 24 | 4-methoxy-phenyl | methoxy | H | 4-Cl-phenyl | H | 1 |
| 213a | 25 | 4-(4-Cl-phenoxy)-phenyl | H | H | phenyl | H | 1 |
| 213b | 26 | 4-(4-Cl-phenoxy)-phenyl | H | H | phenyl | H | 1 |
| 214a | 27 | 4-(4-Cl-phenoxy)-phenyl | methoxy | H | 2-furanyl | H | 1 |
| 214b | 28 | 4-(4-Cl-phenoxy)-phenyl | methoxy | H | 2-furanyl | H | 1 |
| 215a | 29 | 4-(4-Cl-phenoxy)-phenyl | H | O-TBDMS | H | H | 1 |
| 215b | 30 | 4-(4-Cl-phenoxy)-phenyl | H | O-TBDMS | H | H | 1 |

*Mixture of 4 isomers.

TABLE 2

Compounds of general formula (III)

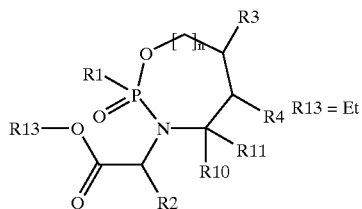

R13 = Et

| Comp No. | Prep No. | R1 | R2 | R3 | R4 | R10 | R11 | n |
|---|---|---|---|---|---|---|---|---|
| 301a | 100 | 4-methoxy-phenyl | H | H | H | phenyl | H | 0 |
| 301b | 101 | 4-methoxy-phenyl | H | H | H | phenyl | H | 0 |
| 302a | 102 | 4-(4-Cl-phenoxy)-phenyl | H | H | H | phenyl | H | 0 |
| 302b | 103 | 4-(4-Cl-phenoxy)-phenyl | H | H | H | phenyl | H | 0 |
| 303a | 104 | phenyl | H | H | H | phenyl | H | 0 |
| 303b | 105 | phenyl | H | H | H | phenyl | H | 0 |
| 304a | 106 | 4-(4-Cl-phenoxy)-phenyl | H | H | H | 4-methoxy-phenyl | H | 0 |
| 304b | 107 | 4-(4-Cl-phenoxy)-phenyl | H | H | H | 4-methoxy-phenyl | H | 0 |
| 305a | 108 | 4-methoxy-phenyl | H | H | H | 4-methoxy-phenyl | H | 0 |
| 305b | 109 | 4-methoxy-phenyl | H | H | H | 4-methoxy-phenyl | H | 0 |
| 306a | 110 | 4-methoxy-phenyl | H | H | H | isopropyl | H | 1 |
| 306b | 111 | 4-methoxy-phenyl | H | H | H | isopropyl | H | 1 |
| 307 | 112 | 4-(4-Cl-phenoxy)-phenyl | H | H | H | isopropyl | H | 1 |
| 308a | 113 | 4-methoxy-phenyl | H | H | H | isobutyl | H | 1 |
| 308b | 114 | 4-methoxy-phenyl | H | H | H | isobutyl | H | 1 |
| 309* | 115 | 4-(4-Cl-phenoxy)-phenyl | H | H | H | isobutyl | H | 1 |
| 310 | 116 | 4-(4-Cl-phenoxy)-phenyl | H | H | H | methyl | methyl | 1 |
| 311a | 117 | 4-(4-Cl-phenoxy)-phenyl | H | methoxy | H | 4-Cl-phenyl | H | 1 |
| 311b | 118 | 4-(4-Cl-phenoxy)-phenyl | H | methoxy | H | 4-Cl-phenyl | H | 1 |
| 311c | 119 | 4-(4-Cl-phenoxy)-phenyl | H | methoxy | H | 4-Cl-phenyl | H | 1 |
| 311d | 120 | 4-(4-Cl-phenoxy)-phenyl | H | methoxy | H | 4-Cl-phenyl | H | 1 |
| 312a | 121 | 4-methoxy-phenyl | H | methoxy | H | 4-Cl-phenyl | H | 1 |
| 312b | 122 | 4-methoxy-phenyl | H | methoxy | H | 4-Cl-phenyl | H | 1 |
| 312c | 123 | 4-methoxy-phenyl | H | methoxy | H | 4-Cl-phenyl | H | 1 |
| 312d | 124 | 4-methoxy-phenyl | H | methoxy | H | 4-Cl-phenyl | H | 1 |
| 313a | 125 | 4-(4-Cl-phenoxy)-phenyl | H | H | H | phenyl | H | 1 |
| 313b | 126 | 4-(4-Cl-phenoxy)-phenyl | H | H | H | phenyl | H | 1 |
| 314* | 127 | 4-methoxy-phenyl | H | H | H | methyl | H | 1 |
| 315* | 128 | 4-(4-Cl-phenoxy)-phenyl | H | H | H | methyl | H | 1 |
| 316* | 129 | 4-methoxy-phenyl | H | H | H | 4-Cl-benzyl | H | 1 |
| 317 | 130 | 4-(4-Cl-phenoxy)-phenyl | H | H | H | 4-Cl-benzyl | H | 1 |
| 318 | 131 | 4-methoxy-phenyl | H | H | H | methyl | H | 2 |

TABLE 2-continued

Compounds of general formula (III)

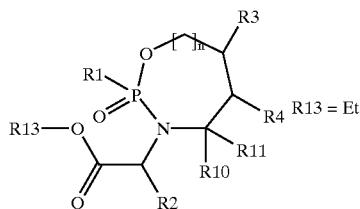

R13 = Et

| Comp No. | Prep No. | R1 | R2 | R3 | R4 | R10 | R11 | n |
|---|---|---|---|---|---|---|---|---|
| 319 | 132 | 4-(4-Cl-phenoxy)-phenyl | H | H | H | methyl | H | 2 |
| 320 | 133 | 4-methoxy-phenyl | methyl | H | H | methyl | H | 1 |
| 321 | 134 | 4-(4-Cl-phenoxy)-phenyl | methyl | H | H | methyl | H | 1 |
| 322a | 135 | 4-(4-Cl-phenoxy)-phenyl | H | methoxy | H | 2-furanyl | H | 1 |
| 322b | 136 | 4-(4-Cl-phenoxy)-phenyl | H | methoxy | H | 2-furanyl | H | 1 |
| 323a | 137 | 4-(4-Cl-phenoxy)-phenyl | H | H | O-TBDMS | H | H | 1 |
| 323b | 138 | 4-(4-Cl-phenoxy)-phenyl | H | H | O-TBDMS | H | H | 1 |
| 324b | 139 | 4-(4-Cl-phenoxy)-phenyl | H | H | OH | H | H | 1 |

*Mixture of 4 isomers

TABLE 3

Compounds of general formula (II)

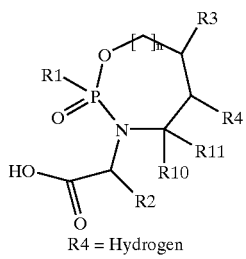

R4 = Hydrogen

| Comp No. | Ex. No | R1 | R2 | R3 | R10 | R11 | n |
|---|---|---|---|---|---|---|---|
| 401a | 200 | 4-(4-Cl-phenoxy)-phenyl | H | H | phenyl | H | 0 |
| 401b | 201 | 4-(4-Cl-phenoxy)-phenyl | H | H | phenyl | H | 0 |
| 402a | 202 | 4-(4-Cl-phenoxy)-phenyl | H | H | 4-methoxy-phenyl | H | 0 |
| 403b | 203 | 4-methoxy-phenyl | H | H | 4-methoxy-phenyl | H | 0 |
| 404 | 204 | 4-(4-Cl-phenoxy)-phenyl | H | H | methyl | methyl | 1 |
| 405a | 205 | 4-(4-Cl-phenoxy)-phenyl | H | methoxy | 4-Cl-phenyl | H | 1 |
| 405b | 206 | 4-(4-Cl-phenoxy)-phenyl | H | methoxy | 4-Cl-phenyl | H | 1 |
| 405c | 207 | 4-(4-Cl-phenoxy)-phenyl | H | methoxy | 4-Cl-phenyl | H | 1 |
| 405d | 208 | 4-(4-Cl-phenoxy)-phenyl | H | methoxy | 4-Cl-phenyl | H | 1 |
| 406a | 209 | 4-methoxy-phenyl | H | methoxy | 4-Cl-phenyl | H | 1 |
| 406b | 210 | 4-methoxy-phenyl | H | methoxy | 4-Cl-phenyl | H | 1 |

TABLE 3-continued

Compounds of general formula (II)

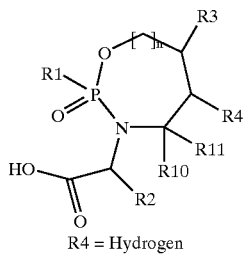

R4 = Hydrogen

| Comp No. | Ex. No | R1 | R2 | R3 | R10 | R11 | n |
|---|---|---|---|---|---|---|---|
| 406c | 211 | 4-methoxy-phenyl | H | methoxy | 4-Cl-phenyl | H | 1 |
| 406d | 212 | 4-methoxy-phenyl | H | methoxy | 4-Cl-phenyl | H | 1 |
| 407a | 213 | 4-(4-Cl-phenoxy)-phenyl | H | H | phenyl | H | 1 |
| 407b | 214 | 4-(4-Cl-phenoxy)-phenyl | H | H | phenyl | H | 1 |
| 408b | 215 | 4-(4-Cl-phenoxy)-phenyl | H | methoxy | 2-furanyl | H | 1 |
| 409 | 216 | 4-methoxy-phenyl | methyl | H | methyl | H | 1 |
| 410 | 217 | 4-(4-Cl-phenoxy)-phenyl | methyl | H | methyl | H | 1 |

TABLE 4

Compounds of formula Ia

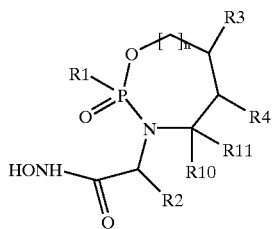

| Comp No. | Ex. No | R1 | R2 | R3 | R4 | R10 | R11 | n |
|---|---|---|---|---|---|---|---|---|
| 101a | 1 | 4-methoxy-phenyl | H | H | H | phenyl | H | 0 |
| 101b | 2 | 4-methoxy-phenyl | H | H | H | phenyl | H | 0 |
| 102a | 3 | 4-(4-Cl-phenoxy)-phenyl | H | H | H | phenyl | H | 0 |
| 102b | 4 | 4-(4-Cl-phenoxy)-phenyl | H | H | H | phenyl | H | 0 |
| 103a | 5 | phenyl | H | H | H | phenyl | H | 0 |
| 103b | 6 | phenyl | H | H | H | phenyl | H | 0 |
| 104a | 7 | 4-(4-Cl-phenoxy)-phenyl | H | H | H | 4-methoxy-phenyl | H | 0 |
| 104b | 8 | 4-(4-Cl-phenoxy)-phenyl | H | H | H | 4-methoxy-phenyl | H | 0 |
| 105a | 9 | 4-methoxy-phenyl | H | H | H | 4-methoxy-phenyl | H | 0 |
| 105b | 10 | 4-methoxy-phenyl | H | H | H | 4-methoxy-phenyl | H | 0 |
| 106b | 11 | 4-methoxy-phenyl | H | H | H | isopropyl | H | 1 |
| 107a | 12 | 4-(4-Cl-phenoxy)-phenyl | H | H | H | isopropyl | H | 1 |
| 107b | 13 | 4-(4-Cl-phenoxy)-phenyl | H | H | H | isopropyl | H | 1 |

TABLE 4-continued

Compounds of formula Ia

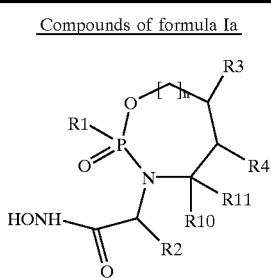

| Comp No. | Ex. No | R1 | R2 | R3 | R4 | R10 | R11 | n |
|---|---|---|---|---|---|---|---|---|
| 108b | 14 | 4-methoxy-phenyl | H | H | H | isobutyl | H | 1 |
| 109a | 15 | 4-(4-Cl-phenoxy)-phenyl | H | H | H | isobutyl | H | 1 |
| 109b | 16 | 4-(4-Cl-phenoxy)-phenyl | H | H | H | isobutyl | H | 1 |
| 110 | 17 | 4-(4-Cl-phenoxy)-phenyl | H | H | H | methyl | methyl | 1 |
| 111a | 18 | 4-(4-Cl-phenoxy)-phenyl | H | methoxy | H | 4-Cl-phenyl | H | 1 |
| 111b | 19 | 4-(4-Cl-phenoxy)-phenyl | H | methoxy | H | 4-Cl-phenyl | H | 1 |
| 111c | 20 | 4-(4-Cl-phenoxy)-phenyl | H | methoxy | H | 4-Cl-phenyl | H | 1 |
| 111d | 21 | 4-(4-Cl-phenoxy)-phenyl | H | methoxy | H | 4-Cl-phenyl | H | 1 |
| 112a | 22 | 4-methoxy-phenyl | H | methoxy | H | 4-Cl-phenyl | H | 1 |
| 112b | 23 | 4-methoxy-phenyl | H | methoxy | H | 4-Cl-phenyl | H | 1 |
| 112c | 24 | 4-methoxy-phenyl | H | methoxy | H | 4-Cl-phenyl | H | 1 |
| 112d | 25 | 4-methoxy-phenyl | H | methoxy | H | 4-Cl-phenyl | H | 1 |
| 113a | 26 | 4-(4-Cl-phenoxy)-phenyl | H | H | H | phenyl | H | 1 |
| 113b | 27 | 4-(4-Cl-phenoxy)-phenyl | H | H | H | phenyl | H | 1 |
| 114* | 28 | 4-methoxy-phenyl | H | H | H | methyl | H | 1 |
| 115* | 29 | 4-(4-Cl-phenoxy)-phenyl | H | H | H | methyl | H | 1 |
| 116* | 30 | 4-methoxy-phenyl | H | H | H | 4-Cl-benzyl | H | 1 |
| 117* | 31 | 4-(4-Cl-phenoxy)-phenyl | H | H | H | 4-Cl-benzyl | H | 1 |
| 118 | 32 | 4-methoxy-phenyl | H | H | H | methyl | H | 2 |
| 119 | 33 | 4-(4-Cl-phenoxy)-phenyl | H | H | H | methyl | H | 2 |
| 120 | 34 | 4-methoxy-phenyl | methyl | H | H | methyl | H | 1 |
| 121 | 35 | 4-(4-Cl-phenoxy)-phenyl | methyl | H | H | methyl | H | 1 |
| 122b | 36 | 4-(4-Cl-phenoxy)-phenyl | H | methoxy | H | 2-furanyl | H | 1 |
| 123a | 37 | 4-(4-Cl-phenoxy)-phenyl | H | H | hydroxy | H | H | 1 |
| 123b | 38 | 4-(4-Cl-phenoxy)-phenyl | H | H | hydroxy | H | H | 1 |

*Mixture of 4 isomers

General Procedure 1: Formation of Hydroxamic Acids of General Formula (Ia) from the Corresponding Carboxylic Acids of General Formula (II)

A solution of carboxylic acid with general formula (II) (2.9 mmol) in THF (45 ml) was cooled to −10° C. under argon. NMM (0.3 ml, 3.0 mmol) and isobutyl chloroformate (0.4 ml, 3.0 mmol) were then added with stirring. After stirring overnight at −10° C., O-trimethylsilyl hydroxylamine (0.4 ml, 3.2 mmol) was added, and the mixture was left at −10° C. for 5 h. The mixture was then acidified with 4 M acetic acid, extracted with EtOAc/$H_2O$. The aqueous layer was back-extracted with EtOAc, and the combined organic layers were washed with brine, dried ($MgSO_4$) and concentrated. The residue was purified by chromatography (chloroform/methanol/NH$_3$ (25%)) or crystallisation to afford the hydroxamic acid of general formula (Ia).

General Procedure 2: Formation of Hydroxamic Acids of General Formula (Ia) from the Corresponding Esters of General Formula (III)

To a solution of ester with general formula (III) (0.20 mmol) in dry methanol (2 ml) was added O-trimethylsilyl-hydroxylamine (72 μl, 0.60 mmol) and sodium methoxide (1.4 M, 214 μl, 0.30 mmol). After stirring at rt for 5 hours, the solution was acidified with 4 M AcOH to pH 4, concentrated under reduced pressure and extracted with EtOAc/H$_2$O. The aqueous layer was back-extracted with EtOAc, and the combined organic layers were washed with brine, dried (MgSO$_4$) and concentrated under reduced pressure. The residue was purified by chromatography (chloroform/methanol/NH$_3$ (25% aq.)) or crystallisation to afford the hydroxamic acid of general formula (Ia).

General Procedure 3: Formation of Carboxylic Acids of General Formula (II) from the Corresponding Oxazaphosphacycloalkane Esters of General Formula (III)

A solution of ester with general formula (III) (0.26 mmol) in methanol (2 ml) and aqueous sodium hydroxide (2 M, 2 ml) was stirred overnight at rt, acidified with 4 M AcOH and extracted with EtOAc/H$_2$O. The aqueous phase was back-extracted with EtOAc, and the combined layers were washed with brine, dried (MgSO$_4$) and concentrated under reduced pressure. The residue was purified by chromatography (chloroform/methanol/acetic acid) or by crystallisation to afford the carboxylic acid of general formula (II).

General Procedure 4: Formation of Oxazaphosphacycloalkane Esters of General Formula (III) by Cyclisation of Phosphonyldichlorides of General Formula (IV) with Amino Alcohols of General Formula (V)

A solution of amino alcohol of general formula (V) (0.42 mmol) and NMM (0.85 mmol) in dry CH$_2$Cl$_2$ (20 ml) was cooled to −40° C. under argon, and a solution phosphonyl-dichloride of general formula (IV) (0.42 mmol) in dry CH$_2$Cl$_2$ (10 ml) was added. The mixture was stirred at 0° C. for 1 hour, then at rt overnight. After quenching with water, the aqueous phase was extracted with EtOAc. The aqueous phase was back-extracted with EtOAc. The combined organic layers were washed with brine, dried (MgSO$_4$) and concentrated under reduced pressure. The residue was purified by chromatography (chloroform/methanol) to afford the oxazaphosphacycloalkane ester of general formula (III).

General Procedure 5. Formation of Oxazaphosphacycloalkanes of General Formula (VII) by Cyclisation of Phosphonyldichlorides of General Formula (IV) with Amino Alcohols of General Formula (VI)

A solution of amino alcohol of general formula (VI) (1.0 mmol) and triethylamine (2.2 mmol) in dry CH$_2$Cl$_2$ (25 ml) was cooled 0° C. under argon, and a solution phosphony-idichloride of general formula (IV) (1.1 mmol) in dry CH$_2$Cl$_2$ (2 ml) was added. The mixture was stirred at 0° C. for 1 hour, then at rt overnight. After quenching with water, the aqueous phase was extracted with EtOAc. The aqueous phase was back-extracted thoroughly with EtOAc. The combined organic layers were washed with brine, dried (MgSO$_4$) and concentrated under reduced pressure. The residue was purified by chromatography (pentane/ethyl acetate) or by crystallisation to afford the oxazaphosphacy-cloalkane of general formula (VII).

General Procedure 6. Formation of Oxazaphosphacycloalkane Esters of General Formula (III) by Alkylation of Oxazaphosphacycloalkanes of General Formula (VII) with Bromo- or Iodoacetic Acid Esters of General Formula (VIII)

A solution of oxazaphosphacycloalkane of general formula (VII) (0.76 mmol) in dry THF (4 ml) was cooled to −70° C., and n-butyllithium (0.76 mmol) was added dropwise. The mixture was stirred at −70° C. for 2 hours, followed by a addition of a solution of bromo- or iodoacetic acid ester of general formula (VIII) (1.52 mmol) in dry THF (1.5 ml). The mixture was removed from the cooling bath and stirred at rt for overnight, quenched with water and extracted with EtOAc/H$_2$O. The aqueous phase was back-extracted thoroughly with EtOAc, and the combined organic layers were washed with water and brine, dried (MgSO$_4$) and concentrated under reduced pressure. The residue was purified by chromatography to afford the oxazaphosphacy-cloalkane ester of general formula (III).

Preparation 1: (±)-2-(4-Methoxyphenyl)-2-oxo-4-phenyl-1,3,2-oxazaphosphorinane (Diastereomer 1, Compound 201a)

General Procedure 5.

Starting materials: 3-Amino-3-phenyl-1-propanol and 4-methoxyphenylphosphonic dichloride.

$^{13}$C-NMR (CDCl$_3$) δ 162.5, 142.5, 133.1, 129.0, 128.2, 126.2, 122.3, 114.3, 66.4, 57.1, 55.4, 34.9

Preparation 2: (±)-2-(4-Methoxyphenyl)-2-oxo-4-phenyl-1,3,2-oxazaphosphorinane (Diastereomer 2, Compound 201b)

General Procedure 5.

Starting materials: 3-Amino-3-phenyl-1-propanol and 4-methoxyphenylphosphonic dichloride.

$^{13}$C-NMR (CDCl$_3$) δ 163.0, 143.4, 134.5, 128.9, 128.1, 126.0, 122.0, 113.9, 65.2, 56.0, 55.4, 35.1

Preparation 3: (±)-2-[4-(4-Chlorophenoxy)-phenyl]-2-oxo-4-phenyl-1,3,2-oxazaphosphorinane (Diastereomer 1, Compound 202a)

General Procedure 5.

Starting materials: 3-Amino-3-phenyl-1-propanol and 4-(4-chlorophenoxy)phenylphosphonic dichloride.

$^{13}$C-NMR (CDCl$_3$) δ 160.5, 154.4, 142.4, 133.3, 130.1, 129.6, 129.1, 128.3, 126.2, 125.5, 121.2, 118.1, 66.4, 57.1, 34.8

Preparation 4: (±)-2-[4-(4-Chlorophenoxy)-phenyl]-2-oxo-4-phenyl-1,3,2-oxazaphosphorinane (Diastereomer 2, Compound 202b)

General Procedure 5.

Starting materials: 3-Amino-3-phenyl-1-propanol and 4-(4-chlorophenoxy)phenylphosphonic dichloride.

$^{13}$C-NMR (CDCl$_3$) δ 160.9, 154.3, 143.3, 134.7, 130.1, 129.6, 128.9, 128.1, 126.0, 125.1, 121.3, 117.6, 65.4, 56.1, 34.9

Preparation 5: (±)-2,4-Diphenyl-2-oxo-1,3,2-oxazaphosphorinane
(Diastereomer 1, Compound 203a)

General Procedure 5.

Starting materials: 3-Amino-3-phenyl-1-propanol and phenylphosphonic dichloride.

$^{13}$C-NMR (CDCl$_3$) δ 142.4, 131.9, 131.2, 131.1, 129.0, 128.8, 128.3, 126.2, 66.5, 57.1, 34.9

Preparation 6: (±)-2,4-Diphenyl-2-oxo-1,3,2-oxazaphosphorinane
(Diastereomer 2, Compound 203b)

General Procedure 5.

Starting materials: 3-Amino-3-phenyl-1-propanol and phenylphosphonic dichloride.

$^{13}$C-NMR (CDCl$_3$) δ 143.3, 132.3, 132.3, 128.9, 128.5, 128.2, 126.0, 65.5, 56.1, 34.9

Preparation 7: (±)-2-[4-(4-Chlorophenoxy)-phenyl]-4-(4-methoxyphenyl)-2-oxo-1,3,2-oxazaphosphorinane
(Diastereomer 1, Compound 204a)

General Procedure 5.

Starting materials: 3-Amino-3-(4-methoxyphenyl)-1-propanol and 4-(4-chlorophenoxy)phenylphosphonic dichloride.

hu 1H-NMR (CDCl$_3$) δ 7.79 (m, 2H), 7.35 (m, 4H), 7.06 (dd, 2H), 7.00 (m, 2H), 6.91 (bd, 2H), 4.55–4.35 (m, 2H), 4.14 (m, 1H), 3.81 (s, 3H), 3.24 (bd, 1H), 2.18 (m, 1H), 1.92 (m, 1H)

Preparation 8: (±)-2-[4-(4-Chlorophenoxy)-phenyl]-4-(4-methoxyphenyl)-2-oxo-1,3,2-oxazaphosphorinane
(Diastereomer 2, Compound 204b)

General Procedure 5.

Starting materials: 3-Amino-3-(4-methoxyphenyl)-1-propanol and 4-(4-chlorophenoxy)phenylphosphonic dichloride.

$^{13}$C-NMR (CDCl$_3$) δ 160.9, 159.4, 154.4, 135.4, 134.6, 130.0, 129.6, 127.2, 125.2, 121.2, 117.6, 114.2, 65.5, 55.5, 55.3, 35.0

Preparation 9: (±)-2,4-Bis(4-methoxyphenyl)-2-oxo-1,3,2-oxazaphosphorinane
(Diastereomer 1, Compound 205a)

General Procedure 5.

Starting materials: 3-Amino-3-(4-methoxyphenyl)-1-propanol and 4-methoxyphenylphosphonic dichloride.

$^1$H-NMR (CDCl$_3$) δ 7.76 (m, 2H), 7.36 (m, 2H), 7.01 (m, 2H), 6.92 (m, 2H), 4.43 (m, 1H), 4.39 (m, 1H), 4.12 (m, 1H), 3.87 (s, 3H), 3.82 (s, 3H), 3.16 (bd, 1H), 2.17 (m, 1H), 1.90 (m, 1H)

Preparation 10: (±)-2,4-Bis(4-methoxyphenyl)-2-oxo-1,3,2-oxazaphosphorinane
(Diastereomer 2, Compound 205b)

General Procedure 5.

Starting materials: 3-Amino-3-(4-methoxyphenyl)-1-propanol and 4-methoxyphenylphosphonic dichloride.

$^1$H-NMR (CDCl$_3$) δ 7.92 (m, 2H), 7.28 (m, 2H), 6.98 (m, 2H), 6.88 (m, 2H), 4.70 (m, 2H), 4.33 (m, 1H), 3.86 (s, 3H), 3.80 (s, 3H), 2.75 (bs, 1H), 2.16 (m, 1H), 1.99 (m, 1H)

Preparation 11: (±)-2-(4-Methoxyphenyl)-4-(1-methylethyl)-2-oxo-1,3,2-oxazaphosphorepane
(Diastereomer 1, Compound 206a)

General Procedure 5.

Starting materials: 4-Amino-5-methyl-1-hexanol and 4-methoxyphenylphosphonic dichloride.

$^{13}$C-NMR (CDCl$_3$) δ 162.2, 133.0, 122.6, 113.7, 65.1, 57.2, 55.3, 35.0, 33.8, 29.8, 19.4, 17.3

Preparation 12: (±)-2-(4-Methoxyphenyl)-4-(1-methylethyl)-2-oxo-1,3,2-oxazaphosphorepane
(Diastereomer 2, Compound 206b)

General Procedure 5.

Starting materials: 4-Amino-5-methyl-1-hexanol and 4-methoxyphenylphosphonic dichloride.

$^{13}$C-NMR (CDCl$_3$) δ 162.6, 133.4, 122.3, 114.0, 67.3, 57.1, 55.3, 33.2, 32.9, 29.5, 19.0, 18.5

Preparation 13: (±)-2-[4-(4-Chlorophenoxy)-phenyl]-4-(1-methylethyl)-2-oxo-1,3,2-oxazaphosphorepane
(Mixture of 4 Isomers, Compound 207)

General Procedure 5.

Starting materials: 4-Amino-5-methyl-1-hexanol and 4-(4-chlorophenoxy)phenylphosphonic dichloride.

$^1$H-NMR (CDCl$_3$) δ 7.88–7.73 (m, 2H), 7.37–7.29 (m, 2H), 7.06–6.93 (m, 4H), 4.66–4.00 (m, 2H), 3.30–2.60 (m, 1H), 3.09–2.50 (bs, 1H), 2.07–1.38 (m, 5H), 0.97–0.80 (d, 3H), 0.97–0.80 (d, 3H)

Preparation 14: (±)-2-(4-Methoxyphenyl)-4-(2-methylpropyl)-2-oxo-1,3,2-oxazaphosphorepane
(Mixture of 4 Isomers, Compound 208)

General Procedure 5.

Starting materials: 4-Amino-6-methyl-1-heptanol and 4-methoxyphenylphosphonic dichloride.

$^1$H-NMR (CDCl$_3$) δ 7.85–7.70 (m, 2H), 6.98–6.90 (m, 2H), 4.65–3.40 (m, 3H), 3.83 (s, 3H), 3.0–2.6 (bs, 1H), 2.06–1.73 (m, 3H), 1.70–1.08 (m, 4H), 0.94–0.77 (d, 3H), 0.84–0.50 (d, 3H)

Preparation 15: (±)-2-[4-(4-Chlorophenoxy)-phenyl]-4-(2-methylpropyl)-2-oxo-1,3,2-oxazaphosphorepane
(Mixture of 4 Isomers, Compound 209)

General Procedure 5.

Starting materials: 4-Amino-6-methyl-1-heptanol and 4-(4-chlorophenoxy)phenylphosphonic dichloride.

$^1$H-NMR (CDCl$_3$) δ 7.88–7.75 (m, 2H), 7.36–7.28 (m, 2H), 7.05–6.90 (m, 4H), 4.7–3.4 (m, 3H), 2.84 (bs, 1H), 2.10–1.74 (m, 3H), 1.70–1.09 (m, 4H), 0.94–0.71 (d, 3H), 0.85–0.50 (d, 3H)

Preparation 16: (±)-2-[4-(4-Chlorophenoxy)-phenyl]-4,4-dimethyl-2-oxo-1,3,2-oxazaphosphorepane (Compound 210)

General Procedure 5.

Starting materials: 4-Amino-4-methyl-1-pentanol and 4-(4-chlorophenoxy)phenylphosphonic dichloride.

$^{13}$C-NMR (CDCl$_3$) δ 159.8, 154.7, 133.0, 130.0, 129.3, 127.7, 121.0, 117.7, 65.5, 52.7, 43.5, 33.6, 26.3, 26.2

Preparation 17: (±)-4-(4-Chlorophenyl)-2-[4-(4-chlorophenoxy)-phenyl]-6-methoxy-2-oxo-1,3,2-oxazaphosphorepane
(Diastereomer 1, Compound 211a)

General Procedure 5.

Starting materials: 4-Amino-(4-chlorophenyl)-2-methoxy-1-butanol and 4-(4-chlorophenoxy)phenylphosphonic dichloride.

$^1$H-NMR (CDCl$_3$) δ 7.83 (m, 2H), 7.35 (m, 2H), 7.26 (m, 2H), 7.17 (m, 2H), 7.03 (m, 2H), 6.99 (m, 2H), 4.85 (bt, 1H), 4.44 (m, 1H), 4.25 (m, 1H), 3.72 (m, 1H), 3.41 (s, 3H), 3.07 (bs, 1H), 2.30–2.07 (m, 2H)

Preparation 18: (±)-4-(4-Chlorophenyl)-2-[4-(4-chlorophenoxy)-phenyl]-6-methoxy-2-oxo-1,3,2-oxazaphosphorepane
(Diastereomer 2, Compound 211b)

General Procedure 5.

Starting materials: 4-Amino-(4-chlorophenyl)-2-methoxy-1-butanol and 4-(4-chlorophenoxy)phenylphosphonic dichloride.

$^{13}$C-NMR (CDCl$_3$) δ 160.5, 154.4, 141.4, 133.4, 133.3, 130.1, 130.0, 129.1, 127.4, 124.8, 121.2, 117.8, 75.4, 63.5, 56.4, 49.6, 43.4

Preparation 19: (±)-4-(4-Chlorophenyl)-2-[4-(4-chlorophenoxy)-phenyl]-6-methoxy-2-oxo-1,3,2-oxazaphosphorepane
(Diastereomer 3, Compound 211c)

General Procedure 5.

Starting materials: 4-Amino-(4-chlorophenyl)-2-methoxy-1-butanol and 4-(4-chlorophenoxy)phenylphosphonic dichloride.

$^{13}$C-NMR (CDCl$_3$) δ 160.6, 154.3, 141.0, 133.7, 133.1, 130.1, 129.6, 129.2, 127.3, 121.2, 117.8, 78.3, 65.2, 57.5, 52.1, 43.6

Preparation 20: (±)-4-(4-Chlorophenyl)-2-[4-(4-chlorophenoxy)-phenyl]-6-methoxy-2-oxo-1,3,2-oxazaphosphorepane
(Diastereomer 4, Compound 211d)

General Procedure 5.

Starting materials: 4-Amino-(4-chlorophenyl)-2-methoxy-1-butanol and 4-(4-chlorophenoxy)phenylphosphonic dichloride.

$^{13}$C-NMR (CDCl$_3$) δ 160.9, 154.2, 142.0, 133.9, 133.6, 130.1, 129.7, 129.0, 127.6, 124.5, 121.2, 117.9, 78.8, 67.0, 57.2, 51.6, 40.1

Preparation 21: (±)-4-(4-Chlorophenyl)-2-(4-methoxyphenyl)-6-methoxy-2-oxo-1,3,2-oxazaphosphorepane
(Diastereomer 1, Compound 212a)

General Procedure 5.

Starting materials: 4-Amino-(4-chlorophenyl)-2-methoxy-1-butanol and 4-methoxyphenylphosphonic dichloride.

$^1$H-NMR (CD$_3$OD) δ 7.80 (m, 2H), 7.38 (m, 2H), 7.32 (m, 2H), 7.07 (m, 2H), 4.44 (m, 1H), 4.27 (m, 1H), 3.86 (s, 3H), 3.65 (m, 1H), 3.45 (s, 3H), 2.29 (m, 1H), 2.09 (m, 1H)

Preparation 22: (±)-4-(4-Chlorophenyl)-2-(4-methoxyphenyl)-6-methoxy-2-oxo-1,3,2-oxazaphosphorepane
(Diastereomer 2, Compound 212b)

General Procedure 5.

Starting materials: 4-Amino-(4-chlorophenyl)-2-methoxy-1-butanol and 4-methoxyphenylphosphonic dichloride.

$^{13}$C-NMR (CD$_3$OD) δ 164.4, 143.2, 134.2, 129.8, 129.0, 122.5, 115.2, 76.9, 64.8, 56.6, 55.9, 50.5, 43.9

Preparation 23: (±)-4-(4-Chlorophenyl)-2-(4-methoxyphenyl)-6-methoxy-2-oxo-1,3,2-oxazaphosphorepane
(Diastereomer 3, Compound 212c)

General Procedure 5.

Starting materials: 4-Amino-(4-chlorophenyl)-2-methoxy-1-butanol and 4-methoxyphenylphosphonic dichloride.

$^{13}$C-NMR (CDCl$_3$) δ 162.6, 141.2, 133.6, 132.8, 129.2, 127.3, 121.7, 114.1, 78.4, 65.0, 57.6, 55.3, 52.0, 43.5

Preparation 24: (±)-4-(4-Chlorophenyl)-2-(4-methoxyphenyl)-6-methoxy-2-oxo-1,3,2-oxazaphosphorepane
(Diastereomer 4, Compound 212d)

General Procedure 5.

Starting materials: 4-Amino-(4-chlorophenyl)-2-methoxy-1-butanol and 4-methoxyphenylphosphonic dichloride.

$^{13}$C-NMR (CDCl$_3$) δ 163.0, 142.0, 133.8, 133.6, 129.0, 127.6, 121.4, 114.1, 78.9, 67.0, 57.2, 55.4, 51.4, 40.5

Preparation 25: (±)-2-[4-(4-Chlorophenoxy)-phenyl]-4-phenyl-2-oxo-1,3,2-oxazaphosphorepane
(Diastereomer 1, Compound 213a)

General Procedure 5.

Starting materials: 4-Amino-4-phenyl-1-butanol and 4-(4-chlorophenoxy)phenylphosphonic dichloride.

$^1$H-NMR (DMSO-d$_6$) δ 7.78 (m, 2H), 7.49 (m, 2H), 7.40 (m, 2H), 7.32 (m, 2H), 7.23 (m, 1H), 7.11 (m, 4H), 5.45 (m, 1H), 4.43 (m, 1H), 4.20 (m, 1H), 2.07–1.70 (m, 4H)

Preparation 26: (±)-2-[4-(4-Chlorophenoxy)-phenyl]-4-phenyl-2-oxo-1,3,2-oxazaphosphorepane
(Diastereomer 2, Compound 213b)

General Procedure 5

Starting materials: 4-Amino-4-phenyl-1-butanol and 4-(4-chlorophenoxy)phenylphosphonic dichloride.

$^{13}$C-NMR (CDCl$_3$) δ 160.3, 154.6, 143.3, 133.1, 130.0, 129.4, 129.0, 127.8, 125.7, 125.4, 121.1, 117.9, 65.2, 56.3, 38.6, 29.8

Preparation 27: (±)-2-[4-(4-Chlorophenoxy)-phenyl]-4-(2-furanyl)-6-methoxy-2-oxo-1,3,2-oxazaphosphorepane
(Diastereomer 1, Compound 214a)

General Procedure 5.

Starting materials: 4-Amino-(2-furanyl)-2-methoxy-1-butanol and 4-(4-chlorophenoxy)phenylphosphonic dichloride.

$^1$H-NMR (CDCl$_3$) δ 160.4, 155.1 (d), 154.5, 141.8, 133.5 (d), 130.0, 129.5, 125.4 (d), 121.0, 117.8 (d), 110.2, 105.9, 75.9, 65.2 (d), 56.9, 44.9, 36.1

Preparation 28: (±)-2-[4-(4-Chlorophenoxy)-phenyl]-4-(2-furanyl)-6-methoxy-2-oxo-1,3,2-oxazaphosphorepane
(Diastereomer 2, Compound 214b)

General Procedure 5.

Starting materials: 4-Amino-(2-furanyl)-2-methoxy-1-butanol and 4-(4-chlorophenoxy)phenylphosphonic dichloride.

$^{13}$C-NMR (CDCl$_3$) δ 160.5, 155.0 (d), 154.5, 142.1, 133.3 (d), 130.0, 129.4, 124.8 (d), 121.2, 117.9 (d), 110.3, 105.2, 75.1, 63.7 (d), 56.4, 44.7, 41.2.

Preparation 29: (±)-2-[4-(4-Chlorophenoxy)-phenyl]-5-[tert-butyldimethylsilyloxy]-2-oxo-1,3,2-oxazaphosphorepane
(Diastereomer 1, Compound 215a)

General Procedure 5.

Starting materials: 4-Amino-3-(tert-butyldimethylsilyloxy)-1-butanol and 4-(4-chlorophenoxy)phenylphosphonic dichloride.

$^{13}$C-NMR (CDCl$_3$) δ 160.6 (d), 155.0, 133.6 (d), 130.4, 129.7, 125.4 (d), 121.4, 118.3 (d), 68.4, 59.8 (d), 46.2, 38.4, 26.2, 18.5, −4.3.

Preparation 30: (±)-2-[4-(4-Chlorophenoxy)-phenyl]-5-[tert-butyldimethylsilyloxyl-2-oxo-1,3,2-oxazaphosphorepane
(Diastereomer 2, Compound 215b)

General Procedure 5.

Starting materials: 4-Amino-3-(tert-butyldimethylsilyloxy)-1-butanol and 4-(4-chlorophenoxy)phenylphosphonic dichloride.

$^{13}$C-NMR (CDCl$_3$) δ 160.6 (d), 155.0, 133.5 (d), 130.4, 129.7, 125.8 (d), 121.4, 118.3 (d), 72.6, 61.2 (d), 47.8, 39.4, 26.1, 18.4, −4.3, −4.4.

Preparation 100: (±)-Ethyl 2-(4-methoxyphenyl)-2-oxo-4-phenyl-1,3,2-oxazaphosphorinane-3-acetate
(Diastereomer 1, Compound 301a)

General Procedure 6.

Starting materials: Compound 201a and ethyl iodoacetate.

$^{13}$C-NMR (CDCl$_3$) δ 170.0, 162.8, 139.9, 134.8, 129.0, 127.8, 127.4, 121.5, 113.8, 63.0, 60.8, 60.7, 55.3, 46.2, 34.1, 14.0

Preparation 101: (±)-Ethyl 2-(4-methoxyphenyl)-2-oxo-4-phenyl-1,3,2-oxazaphosphorinane-3-acetate
(Diastereomer 2, Compound 301b)

General Procedure 6.

Starting materials: Compound 201b and ethyl iodoacetate.

$^{13}$C-NMR (CDCl$_3$) δ 170.5, 162.5, 140.8, 133.9, 128.8, 128.0, 127.0, 123.9, 113.9, 65.1, 62.0, 60.9, 55.4, 46.8, 35.7, 14.1

Preparation 102: (±)-Ethyl 2-[4-(4-chlorophenoxy)-phenyl]-2-oxo-4-phenyl-1,3,2-oxazaphosphorinane-3-acetate (Diastereomer 1, Compound 302a)

General Procedure 6.

Starting materials: Compound 202a and ethyl iodoacetate.

$^{13}$C-NMR (CDCl$_3$) δ 169.9, 160.7, 154.4, 139.6, 134.9, 130.0, 129.5, 129.1, 127.9, 127.3, 124.8, 121.2, 117.6, 63.2, 60.8, 60.7, 46.1, 34.0, 14.0

Preparation 103: (±)-Ethyl 2-[4-(4-chlorophenoxy)-phenyl]-2-oxo-4-phenyl-1,3,2-oxazaphosphorinane-3-acetate (Diastereomer 2, Compound 302b)

General Procedure 6.

Starting materials: Compound 202b and ethyl iodoacetate.

$^{13}$C-NMR (CDCl$_3$) δ 170.5, 160.4, 154.5, 140.7, 134.0, 130.0, 129.5, 128.9, 128.1, 127.1, 126.9, 121.1, 117.9, 65.3, 62.1, 60.9, 46.9, 35.7, 14.1

Preparation 104: (±)-Ethyl 2,4-diphenyl-2-oxo-1,3,2-oxazaphosphorinane-3-acetate
(Diastereomer 1, Compound 303a)

General Procedure 6.

Starting materials: Compound 203a and ethyl iodoacetate.

$^{13}$C-NMR (CDCl$_3$) δ 169.9, 139.6, 132.6, 132.1, 130.8, 129.1, 128.3, 127.9, 127.4, 63.3, 60.8, 60.7, 46.1, 33.9, 14.0

Preparation 105: (±)-Ethyl 2,4-diphenyl-2-oxo-1,3,2-oxazaphosphorinane-3-acetate
(Diastereomer 2, Compound 303b)

General Procedure 6.

Starting materials: Compound 203b and ethyl iodoacetate.

$^{13}$C-NMR (CDCl$_3$) δ 170.5, 140.7, 133.1, 131.8, 131.7, 128.8, 128.5, 128.0, 126.9, 65.4, 62.1, 60.9, 46.8, 35.6, 14.1

Preparation 106: (±)-Ethyl 2-[4-(4-chlorophenoxy)-phenyl]-4-(4-methoxyphenyl)-2-oxo-1,3,2-oxazaphosphorinane-3-acetate
(Diastereomer 1, Compound 304a)

General Procedure 6.

Starting materials: Compound 204a and ethyl iodoacetate.

$^{13}$C-NMR (CDCl$_3$) δ 170.0, 160.7, 159.4, 154.4, 134.9, 131.4, 130.0, 129.5, 128.6, 124.9, 121.2, 117.6, 114.4, 63.4, 60.8, 60.1, 55.4, 46.0, 34.1, 14.0

Preparation 107: (±)-Ethyl 2-[4-(4-chlorophenoxy)-phenyl]-4-(4-methoxyphenyl)-2-oxo-1,3,2-oxazaphosphorinane-3-acetate
(Diastereomer 2, Compound 304b)

General Procedure 6.

Starting materials: Compound 204b and ethyl iodoacetate.

$^{13}$C-NMR (CDCl$_3$) δ 170.5, 160.4, 159.4, 154.5, 134.0, 132.4, 130.1, 128.2, 121.1, 117.8, 114.2, 65.4, 61.5, 60.9, 55.3, 46.7, 35.7, 14.1

Preparation 108: (±)-Ethyl 2,4-bis(4-methoxyphenyl)-2-oxo-1,3,2-oxazaphosphorinane-3-acetate (Diastereomer 1, Compound 305a)

General Procedure 6.

Starting materials: Compound 205a and ethyl iodoacetate.

$^{13}$C-NMR (CDCl$_3$) δ 170.1, 162.7, 159.3, 134.8, 131.7, 128.6, 121.6, 114.4, 113.8, 63.2, 60.7, 60.2, 55.3, 46.0, 34.2, 14.0

Preparation 109: (±)-Ethyl 2,4-bis(4-methoxyphenyl)-2-oxo-1,3,2-oxazaphosphorinane-3-acetate (Diastereomer 2, Compound 305b)

General Procedure 6.

Starting materials: Compound 205b and ethyl iodoacetate.

$^{13}$C-NMR (CDCl$_3$) δ 170.6, 162.4, 159.4, 133.9, 132.6, 128.3, 123.8, 114.2, 113.9, 65.2, 61.4, 60.8, 55.4, 55.3, 46.7, 35.8, 14.1

Preparation 110: (±)-Ethyl 2-(4-methoxyphenyl)-4-(1-methylethyl)-2-oxo-1,3,2-oxazaphosphorepane-3-acetate (Diastereomer 1, Compound 306a)

General Procedure 6.
Starting materials: Compound 206a and ethyl iodoacetate.
$^{1}$H-NMR (CDCl$_3$) δ 7.90 (m, 2H), 6.93 (m, 2H), 4.68 (m, 1H), 4.21 (q, 2H), 4.27–3.70 (m, 4H), 3.84 (s, 3H), 2.66 (m, 1H), 2.10–1.40 (m, 4H), 1.29 (t, 3H), 0.81 (d, 3H), 0.58 (d, 3H)

Preparation 111: (±)-Ethyl 2-(4-methoxyphenyl)-4-(1-methylethyl)-2-oxo-1,3,2-oxazaphosphorepane-3-acetate (Diastereomer 2, Compound 306b)

General Procedure 6.
Starting materials: Compound 206b and ethyl iodoacetate.
$^{13}$C-NMR (CDCl$_3$) δ 171.6, 161.8, 132.9, 124.4, 113.5, 68.4, 65.1, 60.9, 55.2, 52.3, 29.4, 29.1, 25.3, 20.8, 20.0, 14.2

Preparation 112: (±)-Ethyl 2-[4-(4-chlorophenoxy)-phenyl]-4-(1-methylethyl)-2-oxo-1,3,2-oxazaphosphorepane-3-acetate (Diastereomer 1, Compound 307)

General Procedure 6.
Starting materials: Compound 207 and ethyl iodoacetate.
$^{13}$C-NMR (CDCl$_3$) δ 171.5, 159.5, 154.9, 133.2, 129.9, 127.7, 120.8, 117.8, 68.5, 65.3, 61.0, 52.3, 29.3, 29.0, 25.2, 20.8, 20.0, 14.2

Preparation 113: (±)-Ethyl 2-(4-methoxyphenyl)-4-(2-methylpropyl)-2-oxo-1,3,2-oxazaphosphorepane-3-acetate (Diastereomer 1, Compound 308a)

General Procedure 6.
Starting materials: Compound 208 and ethyl iodoacetate.
$^{13}$C-NMR (CDCl$_3$) δ 172.8, 162.3, 133.7, 122.0, 113.7, 64.7, 61.0, 55.3, 53.3, 43.1, 42.6, 31.4, 29.5, 24.5, 22.6, 22.0, 14.2

Preparation 114: (±)-Ethyl 2-(4-methoxyphenyl)-4-(2-methylpropyl)-2-oxo-1,3,2-oxazaphosphorepane-3-acetate (Diastereomer 2, Compound 308b)

General Procedure 6.
Starting materials: Compound 208 and ethyl iodoacetate.
$^{13}$C-NMR (CDCl$_3$) δ 171.8, 161.9, 132.9, 124.7, 113.5, 65.2, 61.0, 58.4, 55.3, 51.1, 40.8, 30.8, 25.0, 24.6, 22.7, 21.7, 14.2

Preparation 115: (±)-Ethyl 2-[4-(4-chlorophenoxy)-phenyl]-4-(2-methylpropyl)-2-oxo-1,3,2-oxazaphosphorepane-3-acetate (Mixture of 4 Isomers, Compound 309)

General Procedure 6.
Starting materials: Compound 209 and ethyl iodoacetate.
$^{13}$C-NMR (CDCl$_3$) δ 171.7, 159.6, 154.9, 133.2, 129.9, 129.1, 128.0, 120.8, 117.8, 65.4, 61.1, 58.4, 51.1, 40.8, 30.9, 25.0, 24.6, 22.6, 21.7, 14.2

Preparation 116: (±)-Ethyl 2-[4-(4-chlorophenoxy)-phenyl]-4,4-dimethyl-2-oxo-1,3,2-oxazaphosphorepane-3-acetate (Compound 310)

General Procedure 6.
Starting materials: Compound 210 and ethyl iodoacetate.
$^{13}$C-NMR (CDCl$_3$) δ 173.2, 159.7, 154.7, 133.2, 129.9, 128.3, 121.0, 117.7, 64.4, 61.0, 57.1, 46.0, 37.8, 29.1, 27.2, 25.6, 14.2

Preparation 117: (±)-Ethyl 4-(4-chlorophenyl)-2-[4-(4-chlorophenoxy)-phenyl]-6-methoxy-2-oxo-1,3,2-oxazaphosphorepane-3-acetate (Diastereomer 1, Compound 311a)

General Procedure 6.
Starting materials: Compound 211a and ethyl iodoacetate.
$^{13}$C-NMR (CDCl$_3$) δ 171.1, 160.3, 154.5, 140.7, 133.4, 133.4, 130.1, 129.6, 128.8, 128.2, 127.8, 121.1, 118.1, 76.4, 64.0, 61.2, 57.8, 57.4, 49.4, 36.0, 14.2

Preparation 118: (±)-Ethyl 4-(4-chlorophenyl)-2-[4-(4-chlorophenoxy)-phenyl]-6-methoxy-2-oxo-1,3,2-oxazaphosphorepane-3-acetate (Diastereomer 2, Compound 311b)

General Procedure 6.
Starting materials: Compound 211b and ethyl iodoacetate.
$^{13}$C-NMR (CDCl$_3$) δ 171.7, 160.5, 154.5, 137.2, 134.2, 133.9, 130.0, 129.8, 129.5, 128.6, 124.7, 121.2, 117.9, 75.4, 63.2, 60.9, 56.3, 51.9, 44.1, 35.4, 14.0

Preparation 119: (±)-Ethyl 4-(4-chlorophenyl)-2-[4-(4-chlorophenoxy)-phenyl]-6-methoxy-2-oxo-1,3,2-oxazaphosphorepane-3-acetate (Diastereomer 3, Compound 311c)

General Procedure 6.
Starting materials: Compound 211c and ethyl iodoacetate.
$^{13}$C-NMR (CDCl$_3$) δ 171.0, 160.6, 154.4, 136.8, 134.2, 134.1, 134.1, 130.1, 129.8, 128.6, 124.2, 121.2, 117.8, 78.4, 64.6, 60.9, 57.7, 54.1, 43.7, 35.5, 14.0

Preparation 120: (±)-Ethyl 4-(4-chlorophenyl)-2-[4-(4-chlorophenoxy)-phenyl]-6-methoxy-2-oxo-1,3,2-oxazaphosphorepane-3-acetate (Diastereomer 4, Compound 311d)

General Procedure 6.
Starting materials: Compound 211d and ethyl iodoacetate.
$^{13}$C-NMR (CDCl$_3$) δ 171.6, 160.3, 154.5, 140.4, 133.6, 133.5, 130.1, 128.9, 128.0, 127.4, 121.0, 118.3, 79.1, 65.7, 61.2, 59.6, 56.7, 48.7, 36.8, 14.2

Preparation 121: (±)-Ethyl 4-(4-chlorophenyl)-6-methoxy-2-(4-methoxyphenyl)-2-oxo-1,3,2-oxazaphosphorepane-3-acetate (Diastereomer 1, Compound 312a)

General Procedure 6.
Starting materials: Compound 212a and ethyl iodoacetate.
$^{13}$C-NMR (CDCl$_3$) δ 171.2, 162.3, 140.8, 133.2, 128.8, 128.3, 124.8, 114.1, 76.5, 63.9, 61.1, 57.7, 57.4, 55.4, 49.4, 36.0, 14.2

Preparation 122: (±)-Ethyl 4-(4-chlorophenyl)-6-methoxy-2-(4-methoxyphenyl)-2-oxo-1,3,2-oxazaphosphorepane-3-acetate (Diastereomer 2, Compound 312b)

General Procedure 6.
Starting materials: Compound 212b and ethyl iodoacetate.
$^{13}$C-NMR (CDCl$_3$) δ 171.8, 162.5, 137.3, 133.9, 133.8, 129.8, 128.6, 121.6, 113.9, 75.5, 63.0, 60.8, 56.3, 55.3, 51.8, 44.1, 35.3, 14.0

Preparation 123: (±)-Ethyl 4-(4-chlorophenyl)-6-methoxy-2-(4-methoxyphenyl)-2-oxo-1,3,2-oxazaphosphorepane-3-acetate (Diastereomer 3, Compound 312c)

General Procedure 6.

Starting materials: Compound 212c and ethyl iodoacetate.

$^{13}$C-NMR (CDCl$_3$) δ 171.1, 162.6, 137.0, 133.9, 129.8, 128.6, 121.2, 114.0, 78.5, 64.5, 60.8, 57.6, 55.4, 54.0, 43.8, 35.4, 14.0

Preparation 124: (±)-Ethyl 4-(4-chlorophenyl)-6-methoxy-2-(4-methoxyphenyl)-2-oxo-1,3,2-oxazaphosphorepane-3-acetate (Diastereomer 4, Compound 312d)

General Procedure 6.

Starting materials: Compound 212d and ethyl iodoacetate.

$^{13}$C-NMR (CDCl$_3$) δ 171.7, 162.4, 140.5, 133.4, 133.3, 128.9, 128.0, 124.3, 114.2, 79.2, 65.5, 61.1, 59.6, 56.7, 55.4, 48.7, 36.7, 14.2

Preparation 125: (±)-Ethyl 2-[4-(4-chlorophenoxy)phenyl]-4-phenyl-2-oxo-1,3,2-oxazaphosphorepane-3-acetate (Diastereomer 1, Compound 313a)

General Procedure 6.

Starting materials: Compound 213a and ethyl iodoacetate.

$^{13}$C-NMR (CDCl$_3$) δ 171.6, 160.0, 154.7, 142.2, 133.5, 130.0, 129.3, 128.5, 127.7, 127.5, 126.9, 120.9, 118.2, 64.0, 63.1, 61.0, 49.2, 31.3, 27.3, 14.2

Preparation 126: (±)-Ethyl 2-[4-(4-chlorophenoxy)phenyl]-4-phenyl-2-oxo-1,3,2-oxazaphosphorepane-3-acetate (Diastereomer 2, Compound 313b)

General Procedure 6.

Starting materials: Compound 213b and ethyl iodoacetate.

$^{13}$C-NMR (CDCl$_3$) δ 171.5, 160.3, 154.7, 139.0, 134.2, 130.0, 129.4, 128.4, 128.0, 125.2, 121.0, 117.9, 64.9, 60.6, 58.4, 44.0, 29.7, 29.6, 14.0

Preparation 127: (±)-Ethyl 2-(4-methoxyphenyl)-4-methyl-2-oxo-1,3,2-oxazaphosphorepane-3-acetate (Mixture of 4 Isomers, Compound 314)

General Procedure 4.

Starting materials: 4-Methoxyphenylphosphonic dichloride and (±)-N-(4-hydroxy-1-methylbutyl)glycine ethyl ester $^1$H-NMR (CDCl$_3$) δ 8.00–7.70 (m, 2H), 7.00–6.85 (m, 2H), 4.55 (m, 1H), 4.39 (dd, 1H), 4.30–3.14 (m, 3H), 4.19 (m, 2H), 3.83 (s, 3H), 2.15–1.35 (m, 4H), 1.27 (t, 3H), 1.17–1.05 (d, 3H)

Preparation 128: (±)-Ethyl 2-[4-(4-chlorophenoxy)phenyl]-4-methyl-2-oxo-1,3,2-oxazaphosphorepane-3-acetate (Mixture of 4 Isomers, Compound 315)

General Procedure 4

Starting materials: 4-(4-Chlorophenoxy)phenylphosphonic dichloride and (±)-N-(4-hydroxy-1-methylbutyl)glycine ethyl ester $^1$H-NMR (CDCl$_3$) δ 8.05–7.85 (m, 2H), 7.32 (m, 2H), 7.07–6.90 (m, 4H), 4.55 (m, 1H), 4.43 (dd, 1H), 4.19 (m, 3H), 3.92–3.65 (dd, 1H), 3.50–3.15 (m, 1H), 2.15–1.45 (m, 4H), 1.26 (t, 3H), 1.20–1.05 (d, 3H)

Preparation 129: (±)-Ethyl 4-(4-chlorophenylmethyl)-2-(4-methoxyphenyl)-2-oxo-1,3,2-oxazaphosphorepane-3-acetate (Mixture of 4 Isomers, Compound 316)

General Procedure 4

Starting materials: 4-Methoxyphenylphosphonic dichloride and (±)-N-(4-hydroxy-1-(4-chlorophenylmethyl)butyl)glycine ethyl ester.

$^1$H-NMR (CDCl$_3$) δ 7.85 (m, 2H), 7.25–6.70 (m, 6H), 4.60 (m, 1H), 4.50-4.30 (dd, 1H), 4.30–3.75 (m, 7H), 3.45–3.15 (m, 1H), 2.90 (m, 1H), 2.80–2.40 (dd, 1H), 2.20-1.50 (m, 4H), 1.35–1.20 (t, 3H).

Preparation 130: (±)-Ethyl 4-(4-chlorophenylmethyl)-2-[4-(4-chlorophenoxy)phenyl]-2-oxo-1,3,2-oxazaphosphorepane-3-acetate (Mixture of 4 Isomers, Compound 317)

General Procedure 4

Starting materials: 4-(4-Chlorophenoxy)phenylphosphonic dichloride and (±)-N-(4-hydroxy-1-(4-chlorophenylmethyl)butyl)glycine ethyl ester.

MS (EI+): 547 (M$^+$, 0.5%), 474 (10%), 422 (100%).

Preparation 131: (±)-Ethyl 2-(4-methoxyphenyl)-4-methyl-2-oxo-1,3,2-oxazaphosphorocane-3-acetate (Compound 318)

General Procedure 4

Starting materials: 4-Methoxyphenylphosphonic dichloride and (±)-N-(5-hydroxy-1-methylpentyl)glycine ethyl ester.

Preparation 132: (±)-Ethyl 2-[4-(4-chlorophenoxy)phenyl]-4-methyl-2-oxo-1,3,2-oxazaphosphorocane-3-acetate (Compound 319)

General Procedure 4

Starting materials: 4-(4-Chlorphenoxy)phenylphosphonic dichloride and (±)-N-(5-hydroxy-1-methylpentyl)glycine ethyl ester.

Preparation 133: (±)-Ethyl 2-(4-methoxyphenyl)-α,4-dimethyl-2-oxo-1,3,2-oxazaphosphorepane-3-acetate (Compound 320)

General Procedure 4

Starting materials: 4-Methoxyphenylphosphonic dichloride and (±)-N-(4-hydroxy-1-methylbutyl)alanine ethyl ester.

Preparation 134: (±)-Ethyl 2-[4-(4-chlorophenoxy)phenyl]-α,4-dimethyl-2-oxo-1,3,2-oxazaphosphorepane-3-acetate (Compound 321)

General Procedure 4

Starting materials: 4-(4-Chlorophenoxy)phenylphosphonic dichloride and (±)-N-(4-hydroxy-1-methylbutyl)alanine ethyl ester.

Preparation 135: (±)-Ethyl 2-[4-(4-chlorophenoxy)phenyl]-4-(2-furanyl)-6-methoxy-2-oxo-1,3,2-oxazaphosphorepane-3-acetate (Diastereomer 1, Compound 322a)

General Procedure 6.

Starting materials: Compound 214a and ethyl iodoacetate.

$^{13}$C-NMR (CDCl$_3$) δ 8.00 (m,2H), 7.40–7.30 (m,3H), 7.05 (m,2H), 7.00 (m,2H), 6.28 (m,1H), 6.14 (m,1H), 4.89

(t,1H), 4.83 (dd,1H), 4.40 (m,1H), 4.00–3.85 (m,3H), 3.67 (dd,1H), 3.58 (m,1H), 3.42 (m,3H), 2.45 (m,1H), 2.23 (m,1H), 0.89 (t,3H).

Preparation 136: (±)-Ethyl 2-[4-(4-chlorophenoxy)-phenyl]-4-(2-furanyl)-6-methoxy-2-oxo-1,3,2-oxazaphosphorepane-3-acetate (Diastereomer 1, Compound 322b)

General Procedure 6.

Starting materials: Compound 214b and ethyl iodoacetate.

$^{13}$C-NMR (CDCl$_3$) δ 171.6, 160.3 (d), 154.7, 152.7 (d), 142.5, 133.8 (d), 130.0, 129.3, 124.5 (d), 121.1, 117.8 (d), 110.2, 108.9, 75.1, 63.5 (d), 60.9, 56.3, 48.0 (d), 44.6 (d), 34.9, 14.1.

Preparation 137: (±)-Ethyl 5-(tert-butyldimethylsilyloxy)-2-[4-(4-chlorophenoxy)-phenyl]-2-oxo-1,3,2-oxazaphosphorepane-3-acetate (Diastereomer 1, Compound 323a)

General Procedure 6.

Starting materials: Compound 215a and ethyl bromoacetate.

$^{13}$C-NMR (CDCl$_3$) δ 172.3, 160.5 (d), 155.0, 134.0 (d), 130.3, 129.7, 125.2 (d), 121.5, 118.1 (d), 69.6, 61.2, 60.2 (d), 51.2 (d), 50.9 (d), 38.2, 26.2, 18.4, 14.6, −4.5.

Preparation 138: (±)-Ethyl 5-(tert-butyldimethylsilyloxy)-2-[4-(4-chlorophenoxy)-phenyl]-2-oxo-1,3,2-oxazaphosphorepane-3-acetate (Diastereomer 2, Compound 323b)

General Procedure 6.

Staring materials: Compound 215b and ethyl bromoacetate.

$^{13}$C-NMR (CDCl$_3$) δ 171.0, 160.1 (d), 154.3, 133.3 (d), 129.8, 129.2, 124.3 (d), 120.9, 117.6 (d), 68.0, 61.0, 60.8 (d), 54.2 (d), 49.7 (d), 38.6, 25.5, 17.8, 14.0, −5.0, −5.1.

Preparation 139: (±)-Ethyl 2-[4-(4-chlorophenoxy)-phenyl]-5-hydroxy-2-oxo-1,3,2-oxazaphosphorepane-3-acetate (Diastereomer 2, Compound 324b)

Procedure: Compound 323b was treated with TBAF (1 eq.) in THF at 60° C. for 1.5 hours. The reaction mixture was cooled to rt, diluted with EtOAc, washed with water and brine, dried and concentrated in vacuo. Flash chromatography afforded the title compound.

$^{13}$C NMR (CDCl$_3$) δ 171.3 (d), 160.6 (d), 154.4, 133.6 (d), 130.0, 129.5, 124.0 (d), 121.2, 117.7 (d), 67.4, 61.3, 61.1 (d), 53.8 (d), 49.7 (d), 38.3, 14.2.

Example 200

(±)-2-[4-(4-Chlorophenoxy)-phenyl]-2-oxo-4-phenyl-1,3,2-oxazaphosphorinane-3-acetic acid (Diastereomer 1, Compound 401a)

General Procedure 3.

Starting materials: Compound 302a.

$^1$H-NMR (CDCl$_3$) δ 7.87 (m, 2H), 7.43 (bd, 2H), 7.35–7.25 (m, 4H), 7.21 (bt, 1H), 6.99–6.88 (m, 4H), 6.16 (bs, 1H), 4.82 (m, 1H), 4.34 (m, 1H), 4.15 (m, 1H), 3.67 (m, 1H), 3.32 (dd, 1H), 2.48 (m, 1H), 2.07 (m, 1H)

Example 201

(±)-2-[4-(4-Chlorophenoxy)-phenyl]-2-oxo-4-phenyl-1,3,2-oxazaphosphorinane-3-acetic acid (Diastereomer 2, Compound 401b)

General Procedure 3.

Starting materials: Compound 302b.

$^1$H-NMR (DMSO-d$_6$) δ 7.83 (m, 2H), 7.50 (m, 2H), 7.30–6.85 (m, 9H), 4.75 (m, 1H), 4.65 (m, 1H), 4.36 (m, 1H), 3.72 (m, 1H), 2.90 (m, 1H), 2.27 (m, 1H), 2.03 (m, 1H)

Example 202

(±)-2-[4-(4-Chlorophenoxy)-phenyl]-4-(4-methoxyphenyl)-2-oxo-1,3,2-oxazaphosphorinane-3-acetic acid (Diastereomer 1, Compound 402a)

General Procedure 3.

Starting materials: Compound 304a.

$^{13}$C-NMR (CD$_3$OD) δ 173.5, 162.4, 161.0, 156.0, 136.2, 133.1, 131.2, 130.7, 129.7, 125.7, 122.6, 118.8, 115.4, 65.7, 61.5, 55.8, 47.2, 35.3

Example 203

(±)-2,4-Bis(4-methoxyphenyl)-2-oxo-1,3,2-oxazaphosphorinane-3-acetic acid (Diastereomer 1, Compound 403b)

General Procedure 3.

Starting materials: Compound 305b.

$^1$H-NMR (CD$_3$OD) δ 7.84 (m, 2H), 7.10 (dd, 2H), 7.06 (bd, 2H), 6.83 (bd, 2H), 5.00–4.50 (m, 2H), 4.41 (m, 1H), 3.89 (s, 3H), 3.75 (s, 3H), 3.62 (dd, 1H), 3.04 (bt, 1H), 2.25 (m, 2H

Example 204

(±)2-[4-(4-Chlorophenoxy)-phenyl]-4,4-dimethyl-2-oxo-1,3,2-oxazaphosphorepane-3-acetic acid (Compound 404)

General Procedure 3.

Starting materials: Compound 310.

$^{13}$C-NMR (CD$_3$OD) δ 178.5, 161.6, 156.1, 134.6, 131.2, 130.6, 129.5, 122.4, 118.7, 66.1, 58.5, 48.1, 38.7, 28.8, 27.7, 26.5

Example 205

(±)-4-(4-Chlorophenyl)-2-[4-(4-chlorophenoxy)-phenyl]-6-methoxy-2-oxo-1,3,2-oxazaphosphorepane-3-acetic acid (Diastereomer 1, Compound 405a)

General Procedure 3

Starting materials: Compound 311a.

$^1$H-NMR (CD$_3$OD) δ 7.85 (m, 2H), 7.42 (m, 2H), 7.18 (m, 2H), 7.15–7.05 (m, 4H), 6.91 (m, 2H), 5.20 (m, 1H), 4.66 (m, 1H), 4.46 (m, 1H), 3.96 (m, 2H), 3.39 (s, 3H), 3.31 (dd, 1H), 2.41 (m, 1H), 2.02 (m, 1H)

Example 206

(±)-4-(4-Chlorophenyl)-2-[4-(4-chlorophenoxy)-phenyl]-6-methoxy-2-oxo-1,3,2-oxazaphosphorepane-3-acetic acid (Diastereomer 2, Compound 405b)

General Procedure 3.

Starting materials: Compound 311b.

$^{13}$C-NMR (CD$_3$OD) δ 176.6, 162.1, 156.0, 139.2, 135.4, 134.7, 131.2, 131.1, 130.7, 129.6, 125.9, 122.5, 118.8, 77.0, 65.1, 56.6, 53.6, 46.2, 36.3

Example 207

(±)-4-(4-Chlorophenyl)-2-[4-(4-chlorophenoxy)-phenyl]-6-methoxy-2-oxo-1,3,2-oxazaphosphorepane-3-acetic acid (Diastereomer 3, Compound 405c)

General Procedure 3.

Starting materials: Compound 311c.

$^{13}$C-NMR (CD$_3$OD) δ 176.7, 162.4, 155.9, 140.7, 135.6, 134.6, 131.2, 130.8, 129.7, 125.4, 122.6, 118.8, 80.1, 79.5, 68.1, 58.1, 57.3, 37.3

Example 208

(±)-4-(4-Chlorophenyl)-2-[4-(4-chlorophenoxy)-phenyl]-6-methoxy-2-oxo-1,3,2-oxazaphosphorepane-3-acetic acid (Diastereomer 4, Compound 405d)

General Procedure 3.

Starting materials: Compound 311d.

$^1$H-NMR (DMSO-d$_6$) δ 7.79 (m, 2H), 7.50 (m, 2H), 7.24–7.12 (m, 6H), 6.79 (m, 2H), 5.44 (m, 1H), 4.28 (m, 2H), 4.08 (dd, 1H), 3.77 (m, 1H), 3.30 (s, 3H), 2.96 (dd, 1H), 2.02 (bt, 2H)

Example 209

(±)-4-(4-Chlorophenyl)-6-methoxy-2-(4-methoxyphenyl)-2-oxo-1,3,2-oxazaphosphorepane-3-acetic acid (Diastereomer 1, Compound 406a)

General Procedure 3.

Starting materials: Compound 312a.

$^{13}$C-NMR (CD$_3$OD) δ 175.8, 164.3, 142.4, 134.4, 134.3, 129.9, 129.8, 125.2, 115.4, 77.6, 65.7, 58.5, 57.5, 56.0, 50.7, 37.1

Example 210

(±)-4-(4-Chlorophenyl)-6-methoxy-2-(4-methoxyphenyl)-2-oxo-1,3,2-oxazaphosphorepane-3-acetic acid (Diastereomer 2, Compound 406b)

General Procedure 3.

Starting materials: Compound 312b.

$^{13}$C-NMR (CD$_3$OD) δ 175.8, 164.4, 139.1, 135.1, 134.8, 131.1, 129.6, 122.4, 115.1, 77.0, 64.9, 56.6, 56.0, 53.4, 45.5, 36.2

Example 211

(±)-4-(4-Chlorophenyl)-6-methoxy-2-(4-methoxyphenyl)-2-oxo-1,3,2-oxazaphosphorepane-3-acetic acid (Diastereomer 3, Compound 406c)

General Procedure 3.

Starting materials: Compound 312c.

$^{13}$C-NMR (CD$_3$OD) δ 175.8, 164.6, 140.1, 135.2, 134.7, 130.9, 129.6, 122.0, 115.2, 80.0, 67.4, 57.5, 57.2, 56.0, 47.2, 37.0

Example 212

(±)-4-(4-Chlorophenyl)-6-methoxy-2-(4-methoxyphenyl)-2-oxo-1,3,2-oxazaphosphorepane-3-acetic acid (Diastereomer 4, Compound 406d)

General Procedure 3.

Starting materials: Compound 312d.

$^{13}$C-NMR (CD$_3$OD) δ 176.2, 164.3, 142.6, 134.3, 134.3, 129.7, 129.5, 125.4, 115.5, 80.4, 67.3, 60.5, 56.9, 56.1, 50.7, 37.9

Example 213

(±)2-[4-(4-Chlorophenoxy)-phenyl]-4-phenyl-2-oxo-1,3,2-oxazaphosphorepane-3-acetic acid (Diastereomer 1, Compound 407a)

General Procedure 3.

Starting materials: Compound 313a.

$^{13}$C-NMR (CD$_3$OD) δ 177.0, 161.8, 156.2, 143.9, 134.7, 131.2, 130.6, 129.5, 128.5, 128.2, 122.3, 119.2, 65.1, 64.7, 51.3, 32.5, 28.3

Example 214

(±)2-[4-(4-Chlorophenoxy)-phenyl]-4-phenyl-2-oxo-1,3,2-oxazaphosphorepane-3-acetic acid (Diastereomer 1, Compound 407b)

General Procedure 3.

Starting materials: Compound 313b.

$^{13}$C-NMR (CD$_3$OD) δ 176.5, 162.1, 156.1, 141.0, 135.5, 131.2, 130.6, 129.5, 129.4, 128.8, 126.2, 122.5, 118.8, 66.9, 60.5, 46.7, 31.3, 30.5

Example 215

(±)-2-[4-(4-Chlorophenoxy)-phenyl]-4-(2-furanyl)-6-methoxy-2-oxo-1,3,2-oxazaphosphorepane-3-acetic acid (Diastereomer 2, Compound 408b)

General Procedure 3

Starting materials: Compound 322b.

$^{13}$C NMR (CD$_3$OD) δ 175.8, 162.1, 156.1, 154.0 (d), 144.0, 135.0 (d), 131.2, 130.7, 125.5 (d), 122.5, 118.8 (d), 111.3, 110.3, 76.6, 65.1 (d), 56.5, 49.4 (d), 45.9 (d), 35.9.

Example 216

(±)-2-(4-Methoxyphenyl)-α,4-dimethyl-2-oxo-1,3,2-oxazaphosphorepane-3-acetic acid (Compound 409)

General Procedure 3

Starting materials: Compound 320.

Example 217

(±)-2-[4-(4-Chlorophenoxy)-phenyl]-α,4-dimethyl-2-oxo-1,3,2-oxazaphosphorepane-3-acetic acid (Compound 410)

General Procedure 3

Starting materials: Compound 321.

Example 1

(±)-2-(4-Methoxyphenyl)-2-oxo-4-phenyl-1,3,2-oxazaphosphorinane-3-acetohydroxamic Acid (Diastereomer 1, Compound 10a)

General Procedure 2.

Starting materials: Compound 301a.

$^1$H-NMR (DMSO-d$_6$) δ 10.5–9.5 (bs, 1H), 8.5–9.0 (bs, 1H), 7.88 (m, 2H), 7.57 (bd, 2H), 7.43 (bt, 2H), 7.32 (m, 1H), 7.03 (m, 2H), 5.00–4.77 (m, 1H), 4.14 (m, 2H), 3.82 (s, 3H), 3.45 (m, 1H), 2.96 (dd, 1H), 2.54 (m, 1H), 1.95 (db, 1H)

Example 2

(±)-2-(4-Methoxyphenyl)-2-oxo-4-phenyl-1,3,2-oxazaphosphorinane-3-acetohydroxamic Acid
(Diastereomer 2, Compound 10b)

General Procedure 2.

Starting materials: Compound 301b.

$^{13}$C-NMR (DMSO-$d_6$) δ 166.1, 161.8, 141.0, 133.3, 128.5, 127.5, 126.5, 124.3, 114.0, 65.0, 60.7, 55.2, 45.2, 34.8

Example 3

(±)-2-[4-(4-Chlorophenoxy)-phenyl]-2-oxo-4-phenyl-1,3,2-oxazaphosphorinane-3-acetohydroxamic Acid
(Diastereomer 1, Compound 102a)

General Procedure 2.

Starting materials: Compound 302a.

$^1$H-NMR (DMSO-$d_6$) δ 10.5–9.75 (bs, 1H), 9.0–8.5 (bs, 1H), 7.96 (m, 2H), 7.55 (bd, 2H), 7.49 (m, 2H), 7.44 (bt, 2H), 7.33 (m, 1H), 7.15 (m, 2H), 7.08 (dd, 2H), 502–4.80 (m, 1H), 4.15 (m, 1H), 3.51 (m, 1H), 2.98 (dd, 1H), 2.54 (m, 1H), 1.96 (m, 1H)

Example 4

(±)-2-[4-(4-Chlorophenoxy)-phenyl]-2-oxo-4-phenyl-1,3,2-oxazaphosphorinane-3-acetohydroxamic Acid
(Diastereomer 2, Compound 102b)

General Procedure 2.

Starting materials: Compound 302b.

$^1$H-NMR (DMSO-$d_6$) δ 10.5–9.8 (s, 1H), 9.0–8.5 (s, 1H), 7.84 (m, 2H), 7.51 (m, 2H), 7.30–7.10 (m, 7H), 7.02 (m, 2H), 4.66 (m, 2H), 4.36 (m, 1H), 3.67 (dd, 1H), 2.88 (t, 1H), 2.27 (m, 1H), 2.07 (m, 1H)

Example 5

(±)-2,4-Diphenyl-2-oxo-1,3,2-oxazaphosphorinane-3-acetohydroxamic Acid
(Diastereomer 1, Compound 103a)

General Procedure 2.

Starting materials: Compound 303a.

$^{13}$C-NMR (DMSO-$d_6$) δ 164.8, 140.0, 132.1, 131.7, 131.6, 128.6, 128.1, 127.4, 127.0, 63.0, 59.8, 44.3, 33.1

Example 6

(±)-2,4-Diphenyl-2-oxo-1,3,2-oxazaphosphorinane-3-acetohydroxamic Acid
(Diastereomer 2, Compound 103b)

General Procedure 2.

Starting materials: Compound 303b.

$^1$H-NMR (DMSO-$d_6$) δ 10.6–9.80 (bs, 1H), 9.0–8.5 (bs, 1H), 7.83 (m, 2H), 7.56 (m, 3H), 7.21 (m, 3H), 6.97 (dd, 2H), 4.67 (m, 2H), 4.39 (m, 1H), 3.72 (m, 1H), 2.87 (bt, 1H), 2.27 (m, 1H), 2.06 (m, 1H)

Example 7

(±)-2-[4-(4-Chlorophenoxy)-phenyl]-4-(4-methoxyphenyl)-2-oxo-1,3,2-oxazaphosphorinane-3-acetohydroxamic Acid
(Diastereomer 1, Compound 104a)

General Procedure 2.

Starting materials: Compound 304a.

$^{13}$C-NMR (CD$_3$OD) δ 168.0, 162.5, 161.0, 156.0, 136.1, 132.9, 131.8, 131.2, 129.7, 125.5, 122.6, 118.9, 115.4, 65.6, 62.1, 55.8, 45.8, 35.3

Example 8

(±)-2-[4-(4-Chlorophenoxy)-phenyl]-4-(4-methoxyphenyl)-2-oxo-1,3,2-oxazaphosphorinane-3-acetohydroxamic Acid
(Diastereomer 2, Compound 104b)

General Procedure 2.

Starting materials: Compound 304b.

$^1$H-NMR (DMSO-$d_6$) δ 10.6–9.8 (bs, 1H), 9.0–8.5 (bs, 1H), 7.83 (m, 2H), 7.50 (m, 2H), 7.16 (m, 2H), 7.13 (m, 2H), 6.96 (m, 2H), 6.82 (m, 2H), 4.62 (m, 2H), 4.35 (m, 1H), 3.71 (s, 3H), 3.61 (dd, 1H), 2.87 (bt, 1H), 2.21 (m, 1H), 2.07 (m, 1H)

Example 9

(±)-2,4-Bis(4-methoxyphenyl)-2-oxo-1,3,2-oxazaphosphorinane-3-acetohydroxamic Acid
(Diastereomer 1, Compound 105a)

General Procedure 2.

Starting materials: Compound 305a.

$^1$H-NMR (CD$_3$OD) δ 7.92 (m, 2H), 7.46 (m, 2H), 7.05 (dd, 2H), 6.97 (m, 2H), 4.87 (m, 1H), 4.35 (m, 2H), 3.86 (s, 3H), 3.80 (s, 3H), 3.51 (dd, 1H), 3.14 (dd, 1(m, 1H), 2.12 (m, 1H)

Example 10

(±)-2,4-Bis(4-methoxyphenyl)-2-oxo-1,3,2-oxazaphosphorinane-3-acetohydroxamic Acid
(Diastereomer 2, Compound 105b)

General Procedure 2.

Starting materials: Compound 305b.

$^1$H-NMR (CD$_3$OD) δ 7.84 (m, 2H), 7.10 (dd, 2H), 7.06 (m, 2H), 6.83 (m, 2H), 5.00–4.30 (m, 3H), 3.89 (s, 3H), 3.75 (s, 3H), 3.63 (dd, 1H), 3.04 (bt, 1H), 2.26 (m, 2H)

Example 11

(±)-2-(4-Methoxyphenyl)-4-(1-methylethyl)-2-oxo-1,3,2-oxazaphosphorepane-3-acetohydroxamic Acid
(Diastereomer 2, Compound 106b)

General Procedure 2.

Starting materials: Compound 306b.

$^{13}$C-NMR (CDCl$_3$) δ 168.6, 162.5, 133.0, 121.5, 114.0, 69.2, 66.3, 55.3, 53.0, 31.1, 30.3, 24.9, 20.7, 19.7

Example 12

(±)-2-[4-(4-Chlorophenoxy)-phenyl]-4-(1-methylethyl)-2-oxo-1,3,2-oxazaphosphorepane-3-acetohydroxamic Acid
(Diastereomer 1, Compound 107a)

General Procedure 2.

Starting materials: Compound 307.

$^{13}$C-NMR (CD$_3$OD) δ 170.5, 162.0, 156.1, 135.6, 131.2, 130.7, 125.6, 122.4, 118.6, 67.1, 64.6, 43.5, 31.1, 30.5, 29.1, 21.2, 20.9

Example 13

(±)-2-[4-(4-Chlorophenoxy)-phenyl]-4-(1-methylethyl)-2-oxo-1,3,2-oxazaphosphorepane-3-acetohydroxamic Acid
(Diastereomer 2, Compound 107b General Procedure 2.

Starting materials: Compound 307.

$^{13}$C-NMR (CD$_3$OD) δ 169.7, 161.5, 156.2, 134.5, 131.2, 130.5, 127.9, 122.3, 118.8, 69.6, 67.2, 52.3, 30.8, 30.2, 26.2, 21.3, 20.2

Example 14

(±)-2-(4-Methoxyphenyl)-4-(2-methylpropyl)-2-oxo-1,3,2-oxazaphosphorepane-3-acetohydroxamic Acid
(Diastereomer 2, Compound 108b)

General Procedure 2.

Starting materials: Compound 308b.

$^{13}$C-NMR (CDCl$_3$) δ 168.6, 162.5, 133.1, 121.9, 114.0, 66.4, 59.7, 55.4, 52.0, 41.6, 32.5, 24.9, 24.6, 22.7, 22.1

Example 15

(±)-2-[4-(4-Chlorophenoxy)-phenyl]-4-(2-methylpropyl)-2-oxo-1 3,2-oxazaphosphorepane-3-acetohydroxamic Acid
(Diastereomer 1, Compound 109a)

General Procedure 2.

Starting materials: Compound 309.

$^1$H-NMR (CD$_3$OD) δ 8.03 (m, 2H), 7.39 (m, 2H), 7.10–6.98 (m, 4H), 4.64 (m, 1H), 4.16 (m, 1H), 3.87 (dd, 1H), 3.66 (m, 1H), 2.14–1.65 (m, 4H), 1.54 (m, 1H), 1.32 (m, 1H), 1.11 (m, 1H), 0.69 (d, 3H), 0.42 (d, 3H)

Example 16

(±)-2-[4-(4-Chlorophenoxy)-phenyl]-4-(2-methylpropyl)-2-oxo-1,3,2-oxazaphosphorepane-3-acetohydroxamic Acid
(Diastereomer 2, Compound 109b)

General Procedure 2.

Starting materials: Compound 309.

$^{13}$C-NMR (CDCl$_3$) δ 168.3, 160.6, 154.3, 133.3, 130.1, 129.7, 124.7, 121.2, 117.8, 66.5, 60.0, 52.3, 41.7, 32.7, 24.9, 24.7, 22.6, 22.1

Example 17

(±)-2-[4-(4-Chlorophenoxy)-phenyl]-4,4-dimethyl-2-oxo-1,3,2-oxazaphosphorepane-3-acetohydroxamic Acid (Compound 110)

General Procedure 1.

Starting materials: Compound 310.

$^1$H-NMR (CD$_3$OD) δ 8.02 (m, 2H), 7.40 (m, 2H), 7.10–7.00 (m, 4H), 4.69 (m, 1H), 4.26 (m, 1H), 4.11 (dd, 1H), 3.85 (dd, 1H), 2.07 (m, 1H), 1.83 (m, 2H), 1.68 (m, 1H), 1.29 (s, 3H), 1.07 (s, 3H)

Example 18

(±)-4-(4-Chlorophenyl)-2-[4-(4-chlorophenoxy)-phenyl]-6-methoxy-2-oxo-1,3,2-oxazaphosphorepane-3-acetohydroxamic Acid
(Diastereomer 1, Compound 111a)

General Procedure 2.

Starting materials: Compound 311a.

$^{13}$C-NMR (CD$_3$OD) δ 169.3, 162.2, 155.9, 141.6, 134.8, 134.5, 131.3, 130.9, 129.9, 129.8, 127.9, 122.6, 119.2, 77.4, 66.2, 59.0, 57.6, 36.7

Example 19

(±)-4-(4-Chlorophenyl)-2-[4-(4-chlorophenoxy)-phenyl]-6-methoxy-2-oxo-1,3,2-oxazaphosphorepane-3-acetohydroxamic Acid
(Diastereomer 2, Compound 111b)

General Procedure 2.

Starting materials: Compound 311b.

$^{13}$C-NMR (CD$_3$OD) δ 170.0, 162.3, 155.9, 138.7, 135.4, 135.0, 131.3, 131.0, 130.8, 129.8, 125.4, 122.6, 118.9, 76.9, 65.1, 56.6, 53.5, 43.7, 36.2

Example 20

(±)-4-(4-Chlorophenyl)-2-[4-(4-chlorophenoxy)-phenyl]-6-methoxy-2-oxo-1,3,2-oxazaphosphorepane-3-acetohydroxamic Acid
(Diastereomer 3, Compound 111c)

General Procedure 2.

Starting materials: Compound 311c.

$^{13}$C-NMR (CD$_3$OD) δ 169.6, 162.5, 155.9, 138.9, 135.6, 135.0, 131.3, 131.0, 130.9, 129.8, 125.0, 122.7, 118.8, 79.6, 66.7, 57.7, 56.1, 43.9, 36.7

Example 21

(±)-4-(4-Chlorophenyl)-2-[4-(4-chlorophenoxy)-phenyl]-6-methoxy-2-oxo-1,3,2-oxazaphosphorepane-3-acetohydroxamic Acid
(Diastereomer 4, Compound 111d)

General Procedure 2.

Starting materials: Compound 311d.

$^1$H-NMR (CD$_3$OD) δ 7.88 (m, 2H), 7.42 (m, 2H), 7.20–7.05 (m, 6H), 6.78 (m, 2H), 5.49 (m, 1H), 4.41 (dd, 1H), 4.25 (m, 1H), 4.14 (dd, 1H), 3.80 (m, 1H), 3.39 (s, 3H), 3.11 (dd, 1H), 2.30–2.00 (m, 2H)

Example 22

(±)-4-(4-Chlorophenyl)-6-methoxy-2-(4-methoxyphenyl)-2-oxo-1,3,2-oxazaphosphorepane-3-acetohydroxamic Acid
(Diastereomer 1, Compound 112a)

General Procedure 2.

Starting materials: Compound 312a.

$^{13}$C-NMR (CD$_3$OD) δ 169.4, 164.4, 141.7, 134.5, 129.9, 129.8, 124.6, 115.5, 77.5, 66.1, 58.9, 57.6, 56.1, 36.7

Example 23

(±)-4-(4-Chlorophenyl)-6-methoxy-2-(4-methoxyphenyl)-2-oxo-1,3,2-oxazaphosphorepane-3-acetohydroxamic Acid
(Diastereomer 2, Compound 112b)

General Procedure 2.

Starting materials: Compound 312b.

$^{13}$C-NMR (CD$_3$OD) δ 170.2, 164.5, 138.9, 135.0, 131.0, 129.8, 122.1, 115.2, 77.0, 65.0, 56.6, 56.0, 53.5, 43.9, 36.3

Example 24

(±)-4-(4-Chlorophenyl)-6-methoxy-2-(4-methoxyphenyl)-2-oxo-1,3,2-oxazaphosphorepane-3-acetohydroxamic Acid
(Diastereomer 3, Compound 112c)

General Procedure 2.

Starting materials: Compound 312c.

$^{13}$C-NMR (CD$_3$OD) δ 169.7, 164.6, 139.0, 135.2, 135.0, 131.0, 129.8, 121.8, 115.2, 79.7, 66.7, 57.7, 56.1, 56.0, 44.0, 36.6

Example 25

(±)-4-(4-Chlorophenyl)-6-methoxy-2-(4-methoxyphenyl)-2-oxo-1,3,2-oxazaphosphorepane-3-acetohydroxamic Acid
(Diastereomer 4, Compound 112d)

General Procedure 2.

Starting materials: Compound 312d.

$^{13}$C-NMR (CD$_3$OD) δ 169.8, 164.4, 142.2, 134.5, 134.4, 129.8, 129.5, 125.0, 115.5, 80.4, 67.3, 60.8, 57.0, 56.1, 48.2, 37.8

Example 26

(±)-2-[4-(4-Chlorophenoxy)-phenyl]-4-phenyl-2-oxo-1,3,2-oxazaphosphorepane-3-acetohydroxamic Acid (Diastreomer 1, Compound 113a)

General Procedure 2.

Starting materials: Compound 313a.

$^{13}$C-NMR (CD$_3$OD) δ 169.8, 162.0, 156.1, 143.1, 134.8, 131.2, 130.7, 129.6, 128.7, 128.2, 127.9, 122.4, 119.2, 65.3, 65.1, 32.3, 28.2

Example 27

(±)-2-[4-(4-Chlorophenoxy)phenyl]-4-phenyl-2-oxo-1,3,2-oxazaphosphorepane-3-acetohydroxamic Acid
(Diastereomer 2, Compound 113b)

General Procedure 2.

Starting materials: Compound 313b.

$^{13}$C-NMR (CD$_3$OD) δ 170.2, 162.2, 156.0, 140.3, 135.5, 131.2, 130.7, 129.6, 129.4, 129.1, 125.9, 122.5, 118.9, 66.8, 60.0, 43.9, 30.9, 30.5

Example 28

(±)-2-(4-Methoxyphenyl)-4-methyl-2-oxo-1,3,2-oxazaphosphorepane-3-acetohydroxamic Acid
(Mixture of 4 Isomers, Compound 114)

General Procedure 2.

Starting materials: Compound 314.

$^1$H-NMR (CD$_3$OD) δ 7.85 (m, 2H), 7.00 (m, 2H), 4.51 (m, 1H), 4.21 (m, 1H), 3.92 (dd, 1H, 3.84 (s, 3H), 3.69 (dd, 1H), 2.20–1.90 (m, 2H), 1.76 (m, 2H), 1.10 (d, 3H).

Example 29

(±)-2-[4-(4-Chlorophenoxy)-phenyl]-4-methyl-2-oxo-1,3,2-oxazaphosphorepane-3-acetohydroxamic Acid (Mixture of 4 Isomers, Compound 115)

General Procedure 2.

Starting materials: Compound 315.

$^1$H-NMR (DMSO-d$_6$) δ 10.8–9.8 (bs, 1H), 9.2–8.7 (bs, 1H), 8.00–7.80 (m, 2H), 7.47 (m, 2H), 7.11 (m, 2H), 7.04 (m, 2H), 4.35 (m, 1H), 4.07 (m, 2H), 3.88 (dd, 1H), 3.55 (dd, 1H), 1.87 (m, 2H), 1.64 (m, 2H), 0.90–1.10 (d, 3H)

Example 30

(±)-4-(4-Chlorophenylmethyl)-2-(4-methoxyphenyl)-2-oxo-1,3,2-oxazaphosphorepane-3-acetohydroxamic Acid
(Mixture of 4 Isomers, Compound 116)

General Procedure 2.

Starting materials: Compound 316.

$^{13}$C NMR (DMSO-d$_6$) δ 167.1, 161.2, 138.1, 132.5 (d), 130.6, 130.4, 128.2, 124.9 (d), 113.5 (d), 64.3 (d), 55.1, 48.7 (d), 37.0, 29.1, 28.3 (d), 27.8, 24.1.

Example 31

(±)-4-(4-Chlorophenylmethyl)-2-[4-(4-chlorophenoxy)-phenyl]-2-oxo-1,3,2-oxazaphosphorepane-3-acetohydroxamic Acid
(Mixture of 4 Isomers, Compound 117)

General Procedure 2.

Starting materials: Compound 317.

$^1$H-NMR (CD$_3$OD) δ 8.00–7.70 (m, 2H), 7.39 (m, 2H), 7.21 (m, 2H), 7.15–6.90 (m, 6H), 4.56 (m, 1H), 4.29 (m, 1H), 4.03 (m, 1H), 3.83 (m, 1H), 3.50 (m, 1H), 2.88 (m, 1H), 2.75 (m, 1H), 2.16 (m, 1H), 1.95–1.45 (m, 3H)

Example 32

(±)-2-(4-Methoxyphenyl)-4-methyl-2-oxo-1,3,2-oxazaphosphorocane-3-acetohydroxamic Acid (Compound 118)

General Procedure 2.
Starting materials: Compound 318.

Example 33

(±)-2-[4-(4-Chlorophenoxy)-phenyl]-4-methyl-2-oxo-1,3,2-oxazaphosphorocane-3-acetohydroxamic Acid (Compound 119)

General Procedure 2.
Starting materials: Compound 319.

Example 34

(±)-2-(4-Methoxyphenyl)-α,4-dimethyl-2-oxo-1,3,2-oxazaphosphorepane-3-acetohydroxamic Acid (Compound 120)

General Procedure 1.
Starting materials: Compound 409.

Example 35

(±)-2-[4-(4-Chlorophenoxy)-phenyl]-α,4-dimethyl-2-oxo-1,3,2-oxazaphosphorepane-3-acetohydroxamic Acid (Compound 121)

General Procedure 1.
Starting materials: Compound 410.

Example 36

(±)-2-[4-(4-Chlorophenoxy)-phenyl]-4-(2-furanyl)-6-methoxy-2-oxo-1,3,2-oxazaphosphorepane-3-acetohydroxamic Acid (Diastereomer 2, Compound 122b)

General Procedure 2.
Starting materials: Compound 322b.

$^{13}$C-NMR (CD$_3$OD) δ 170.1, 162.2, 156.0, 153.6 (d), 144.2, 135.1 (d), 131.2, 130.7, 125.4 (d), 122.6, 118.8 (d), 111.4, 110.5, 76.5, 65.1 (d), 56.5, 49.3 (d), 44.1 (d), 35.8

Example 37

(±)-2-[4-(4-Chlorophenoxy)-phenyl]-5-hydroxy-2-oxo-1,3,2-oxazaphosphorepane-3-acetohydroxamic Acid (Diastereomer 1, Compound 123a)

Procedure: A solution of Compound 323a in THF was treated with TBAF for 1.5 hours at 60° C. After cooling to rt, the reaction mixture was diluted with EtOAC, washed with water and brine, dried and concentrated in vacuo. The crude mixture was purified by flash chromatography to afford a lactone intermediate, 2-[4-(4-Chlorophenoxy)-phenyl]-2-oxo-3,7-dioxa-1-aza-2λ$^5$-phospha-bicyclo[4.3.1]decan-8-one, which was converted to the title compound by following general procedure 2.

$^{13}$C NMR (DMSO-d$_6$) δ 167.3, 159.1 (d), 154.3, 133.5 (d), 130.0, 128.1, 125.5 (d), 121.2, 117.4 (d), 66.1, 59.6 (d), 51.6 (d), 49.7 (d), 36.7.

Example 38

(±)-2-[4-(4-Chlorophenoxy)-phenyl]-5-hydroxy-2-oxo-1,3,2-oxazaphosphorepane-3-acetohydroxamic Acid (Diastereomer 2, Compound 123b)

General Procedure 2.
Starting material: Compound 324b
MS (ES+): [M+Na]$^+$=449 (100%); (ES−): [M−H]$^−$=425 (100%).

Example 39

Capsules Containing Compound 102a

Compound 102a was dissolved in fractionated coconut oil to a final concentration of 10 mg/ml. Ten parts by weight of gelatine, 5 parts by weight of glycerine, 0.08 parts by weight of potassium sorbate, and 14 parts by weight of distilled water were mixed together with heating and formed into soft gelatine capsules. These were then filled each with 500 μl of the oily solution of Compound 102a.

Example 40

Tablet Containing Compound 102a

| | |
|---|---|
| Compound 102a (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 percent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time.

Tablets with a weight of 200 mg are produced from the granulation by means of a suitable tableting machine.

Example 41

Formulation for Injection Containing Compound 102a

| | |
|---|---|
| Compound 102a (active substance) | 1% |
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilised.

What is claimed is:

1. A compound according to formula I

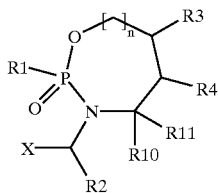

n is 0, 1, 2 and or 3;

X represents hydroxamic acid (CONHOH), carboxylic acid, phosphonic acid, acetylthiomethyl group or a mercaptomethyl group;

R1 is

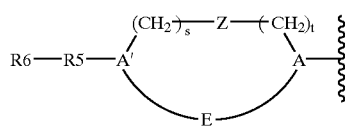

wherein E, when present, represents a bond or optionally substituted methylene or ethylene;

s and t are independently 0, 1, 2 or 3;

A and A' independently represent a bond, or a saturated or unsaturated, optionally substituted cyclic or heterocyclic hydrocarbon di- or triradical;

Z represents a bond, O, S, C(O), C(O)NR7, NR7C(O) or NR7, wherein R7 is hydrogen, hydroxy, branched or straight, saturated or unsaturated, optionally substituted hydrocarbon radical;

R5 represents a bond, alkane or alkene diradical, one or more ether diradicals (R—O—R') or amine diradicals (R—N—R'), wherein R and R' independently represent alkane or alkene diradicals with a C-content from 0 to 3;

R6 represents hydrogen, hydroxy, halogen, cyano, nitro, branched or straight, saturated or unsaturated, optionally substituted hydrocarbon radical, unsaturated optionally substituted cyclic or heterocyclic hydrocarbon radical, NR8R9, C(O)NR8R9, C(O)R8, CO(O)R8, S(O)$_2$R9, wherein each R8 and R9 independently represent hydrogen, halogen, a branched or straight, saturated or unsaturated, optionally substituted hydrocarbon radical;

R2, R10 and R11 independently represent hydrogen or (C$_{1-8}$)alkyl, (C$_{2-6}$)alkenyl, (C$_{3-8}$)cycloalkyl, aryl(C$_{0-6}$) alkyl or heteroaryl(C$_{0-6}$)alkyl, all of which may optionally be substituted;

R3 and R4 independently represent hydrogen, hydroxy or alkoxy;

provided that if A, A', Z and R5 are all bonds, and s and t are both 0 (zero), then R6 is different from hydrogen, and that at least one of R3, R4, R10 and R11 is different from hydrogen;

and a pharmaceutically acceptable salt, hydrate or solvate thereof.

2. A compound according to claim 1 wherein X represents CONHOH.

3. A compound according to claim 1 or 2 wherein n is 0 or 1.

4. A compound according to claim 1 wherein R1 is selected from the group consisting of alkoxyphenyl or phenoxyphenyl optionally substituted with halogen, halogen substituted hydrocarbon radical, cyano, phenylalkyl or naphtylalkyl optionally substituted with halogen, phenyl optionally substituted with halogen or nitro, hydrocarbon radical, biphenyl optionally substituted with halogen, benzylphenoxyl, phenyl-(NH)—C(O)-phenyl optionally substituted with halogen or cyano and methoxy.

5. A compound according to claim 4, wherein R1 is selected from the group consisting of 4-methoxyphenyl, 4-(4-chloro-phenoxy)-phenyl, 4-(4-bromophenoxy)-phenyl, 4-(4-trifluoromethylphenoxy)-phenyl, 4'bromo-4-biphenylyl, N-(4-chlorbenzoyl)-4-aminophenyl, 4-nitrophenyl, N-benzoyl-4-aminophenyl, 4-phenoxyphenyl.

6. A compound according to any of claim 1, wherein R2 is selecetd from the group consisting of hydrogen, (C$_{1-8}$) alkyl, (C$_{2-6}$)alkenyl and aryl(C$_{0-6}$)alkyl.

7. A compound according to claim 6 wherein R2 is selecetd from the group consisting of hydrogen, isopropyl, allyl, isobutyl, n-butyl, n-octyl and benzyl.

8. A compound according to any of claims 1, wherein R3 and R4 are independently hydrogen or methoxy.

9. A compound according to any of claims 1, wherein R10 represents alkyl or optionally substituted phenyl or alkoxyphenyl.

10. A compound according to claim 9, wherein R10 represents phenyl, 4-halo-phenyl and in particular 4-chlorophenyl, 4-methoxyphenyl, methyl, isopropyl and isobutyl.

11. A compound according to any of claims 1, wherein R11 represents hydrogen or alkyl.

12. A compound according to any of claims 1, wherein the C-atom carrying R2 has R configuration.

13. A compound according to claim 1 selected from the group consisting of (±)-2-(4-Methoxyphenyl)-2-oxo-4-phenyl-1,3,2-oxazaphosphorinane-3-acetohydroxamic acid (diastereomer 1), (±)-2-(4-Methoxyphenyl)-2-oxo-4-phenyl-1,3,2-oxazaphosphorinane-3-acetohydroxamic acid (diastereomer 2), (±)-2-[4-(4-Chlorophenoxy)-phenyl]-2-oxo-4-phenyl-1,3,2-oxazaphosphorinane-3-acetohydroxamic acid (diastereomer 1), (±)-2-[4-(4-Chlorophenoxy)-phenyl]-2-oxo-4-phenyl-1,3,2-oxazaphosphorinane-3-acetohydroxamic acid (diastereomer 2), (±)-2,4-Diphenyl-2-oxo-1,3,2-oxazaphosphorinane-3-acetohydroxamic acid (diastereomer 1), (±)-2,4-Diphenyl-2-oxo-1,3,2-oxazaphosphorinane-3-acetohydroxamic acid (diastereomer 2), (±)-2-[4-(4-Chlorophenoxy)-phenyl]-4-(4-methoxyphenyl)-2-oxo-1,3,2-oxazaphosphorinane-3-acetohydroxamic acid (diastereomer 1), (±)-2-[4-(4-Chlorophenoxy)-phenyl]-4-(4-methoxyphenyl)-2-oxo-1,3,2-

(±)-2,4-Bis(4-methoxyphenyl)-2-oxo-1,3,2-oxazaphosphorinane-3-acetohydroxamic acid (diastereomer 1), (±)-2,4-Bis(4-methoxyphenyl)-2-oxo-1,3,2-oxazaphosphorinane-3-acetohydroxamic acid (diastereomer 2), (±)-2-(4-Methoxyphenyl)-4-(1-methylethyl)-2-oxo-1,3,2-oxazaphosphorepane-3-acetohydroxamic acid (diastereomer 2), (±)-2-[4-(4-Chlorophenoxy)-phenyl]-4-(1-methylethyl)-2-oxo-1,3,2-oxazaphosphorepane-3-acetohydroxamic acid (diastereomer 1), (±)-2-[4-(4-Chlorophenoxy)-phenyl]-4-(1-methylethyl)-2-oxo-1,3,2-oxazaphosphorepane-3-acetohydroxamic acid (diastereomer 2), (±)-2-(4-Methoxyphenyl)-4-(2-methylpropyl)-2-oxo-1,3,2-oxazaphosphorepane-3-acetohydroxamic acid (diastereomer 2), (±)-2-[4-(4-Chlorophenoxy)-phenyl]-4-(2-methylpropyl)-2-oxo-1,3,2-oxazaphosphorepane-3-acetohydroxamic acid (diastereomer 1), (±)-2-[4-(4-Chlorophenoxy)-phenyl]-4-(2-methylpropyl)-2-oxo-1,3,2-oxazaphosphorepane-3-acetohydroxamic acid (diastereomer 2), (±)2-[4-(4-Chlorophenoxy)-phenyl]-4,4-dimethyl-2-oxo-1,3,2-oxazaphosphorepane-3-acetohydroxamic acid, (±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 1), (±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 2), (±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 3), (±)-4-(4-Chlorophenyl)-2-[4-(4-chlorophenoxy)-phenyl]-6-methoxy-2-oxo-1,3,2-oxazaphosphorepane-3-acetohydroxamic acid (diastereomer 4)

(±)-4-(4-Chlorophenyl)-6-methoxy-2-(4-methoxyphenyl)-2-oxo-1,3,2-oxazaphosphorepane-3-acetohydroxamic acid (diastereomer 1), (±)-4-(4-Chlorophenyl)-6-methoxy-2-(4-methoxyphenyl)-2-oxo-1,3,2-oxazaphosphorepane-3-acetohydroxamic acid (diastereomer 2), (±)-4-(4-Chlorophenyl)-6-methoxy-2-(4-methoxyphenyl)-2-oxo-1,3,2-oxazaphosphorepane-3-acetohydroxamic acid (diastereomer 3), (±)-4-(4-Chlorophenyl)-6-methoxy-2-(4-methoxyphenyl)-2-oxo-1,3,2-oxazaphosphorepane-3-acetohydroxamic acid (diastereomer 4), (±)2-[4-(4-Chlorophenoxy)-phenyl]-4-phenyl-2-oxo-1,3,2-oxazaphosphorepane-3-acetohydroxamic acid (diastreomer 1), (±)2-[4-(4-Chlorophenoxy)-phenyl]-4-phenyl-2-oxo-1,3,2-oxazaphosphorepane-3-acetohydroxamic acid (diastereomer 2), (±)-2-(4-Methoxyphenyl)-4-methyl-2-oxo-1,3,2-oxazaphosphorepane-3-acetohydroxamic acid (mixture of 4 isomers), (±)-2-(4-Chlorophenoxy)-phenyl]-4-methyl-2-oxo-1,3,2-oxazaphosphorepane-3-acetohydroxamic acid (mixture of 4 isomers), (±)-4-(4-Chlorophenylmethyl)-2-(4-methoxyphenyl)-2-oxo-1,3,2-oxazaphosphorepane-3-acetohydroxamic acid (mixture of 4 isomers)

(±)-4-(4-Chlorophenylmethyl)-2-[4-(4-chlorophenoxy)-phenyl]-2-oxo-1,3,2-oxazaphosphorepane-3-acetohydroxamic acid (mixture of 4 isomers), (±)-2-[4-(4-chlorophenoxy)-phenyl]-4-(2-furanyl)-6-methoxy-2-oxo-1,3,2-oxazaphosphorepane-3-acetohydroxamic acid (diastereomer 2), (±)-2-[4-(4-chlorophenoxy)-phenyl]-5-hydroxy-2-oxo-1,3,2-oxazaphosphorepane-3-acetohydroxamic acid (diastereomer 1), (±)-2-[4-(4-chlorophenoxy)-phenyl]-5-hydroxy-2-oxo-1,3,2-oxazaphosphorepane-3-acetohydroxamic acid (diastereomer 2);

and the corresponding carboxylic acids.

14. An isomer of a compound according to any of claims 1-13 in pure form, or as a mixture of isomers of said compound.

15. A pharmaceutical composition comprising a compound according to claim 1 as an active ingredient, optionally together with other pharmacologically active ingredients, and optionally together with pharmaceutically acceptable carriers.

16. A method for the treatment or prophylaxis of diseases or conditions involving tissue break down, inflammation or proliferative disorders, the method comprising administering to a patient in need thereof an effective amount of a compound according to claim 1.

17. A method according to claim 16, wherein the disease or condition is rheumatoid arthritis, osteoarthritis, osteopenias, osteroporosis, periodontitis, gingivitis, corneal epidermal, gastric ulceration, skin ageing, tumour metastasis, tumour invasion, tumor growth, multiple sclerosis, angiogenesis dependent diseases, arthritic conditions, solid tumour growth, psoriasis, proliferative retinopathies, neovascular glaucoma, ocular tumours, angiofibromas, hemangiomas. asthma, septic shock, fever, cardiovascular effect, haemorrage, coagulation, acute phase reponse, Crohn's disease, mycobacterial infection, meningitis, congestive heart failure or apoptosis.

* * * * *